United States Patent
Townsend et al.

(10) Patent No.: US 11,084,833 B2
(45) Date of Patent: Aug. 10, 2021

(54) ANTIBACTERIAL AGENTS AGAINST D,D- AND L,D-TRANSPEPTIDASES

(71) Applicant: The Johns Hopkins University, Baltimore, MD (US)

(72) Inventors: Craig A. Townsend, Baltimore, MD (US); Evan Lloyd, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 97 days.

(21) Appl. No.: 16/340,244

(22) PCT Filed: Oct. 10, 2017

(86) PCT No.: PCT/US2017/055828
§ 371 (c)(1),
(2) Date: Apr. 8, 2019

(87) PCT Pub. No.: WO2018/071358
PCT Pub. Date: Apr. 19, 2018

(65) Prior Publication Data
US 2020/0040005 A1    Feb. 6, 2020

Related U.S. Application Data

(60) Provisional application No. 62/406,095, filed on Oct. 10, 2016.

(51) Int. Cl.
| | |
|---|---|
| *A61K 31/431* | (2006.01) |
| *A61K 31/43* | (2006.01) |
| *C07D 499/887* | (2006.01) |
| *A61P 31/06* | (2006.01) |
| *A61P 31/04* | (2006.01) |
| *A61K 45/06* | (2006.01) |

(52) U.S. Cl.
CPC .......... *C07D 499/887* (2013.01); *A61K 31/43* (2013.01); *A61K 31/431* (2013.01); *A61K 45/06* (2013.01); *A61P 31/06* (2018.01)

(58) Field of Classification Search
CPC .. A61K 31/431; A61K 31/43; C07D 499/887; A61P 31/06; A61P 31/04
USPC .................. 514/368; 548/170, 169, 165, 178
See application file for complete search history.

(56) References Cited

U.S. PATENT DOCUMENTS

| | | | |
|---|---|---|---|
| 4,619,924 | A | 10/1986 | Hamanaka |
| 4,695,626 | A | 9/1987 | Brighty |
| 7,078,380 | B2 | 7/2006 | Cooper et al. |
| 8,258,127 | B2 | 9/2012 | Mainardi et al. |
| 2005/0004092 | A1* | 1/2005 | Ishiguro ............... C07D 499/88 514/192 |
| 2007/0154948 | A1 | 7/2007 | Christensen et al. |
| 2018/0263969 | A1 | 9/2018 | Patel et al. |

FOREIGN PATENT DOCUMENTS

| | | |
|---|---|---|
| EP | 0110280 | 6/1984 |
| EP | 0126587 | 11/1984 |
| EP | 0130025 | 1/1985 |
| EP | 0162193 | 11/1985 |
| EP | 0226304 | 6/1987 |
| EP | 0774465 | 5/1997 |
| EP | 1375492 | 3/2002 |
| JP | S57-176988 | 10/1982 |
| JP | H0812676 | 1/1996 |
| WO | WO 1983/002614 | 8/1983 |
| WO | WO 1994/006803 | 3/1994 |
| WO | WO 2018/071358 | 4/2018 |

OTHER PUBLICATIONS

Afonine et al., Towards automated crystallographic structure refinement with phenix.refine. Acta Crystallogr D Biol Crystallogr. Apr. 2012;68(Pt 4):352-67.
Albers-Schonberg et al., Structure and Absolute Configuration of Thienamycin. J Am Chem Soc. 1978;100(20):6491-6499.
Baxter et al., Synthesis of 7-Oxo-1-azabicyclo [3.2.0] hept-2-ene-2-carboxylates: the Olivanic Acid Ring System. J C S Chem Comm. 1979: 236-7.
Bernard et al., A New Entry to Alkylidenecyclopropanes Through a Ramberg-Backlund Rearrangement of Cyclopropylsulfones. Synth Commun. 2003;33(5):801-817.
Brammer Basta et al., Loss of a Functionally and Structurally Distinct ld-Transpeptidase, LdtMt5, Compromises Cell Wall Integrity in *Mycobacterium tuberculosis*. J Biol Chem. Oct. 16, 2015;290(42):25670-85.
Brenek, et al., Development of a practical and convergent process for the preparation of sulopenem. Org Process Res Dev. Jul. 2012; 16(8): 1348-1359.
Cama et al., Total Synthesis of Thienamycin Analogues. 1. Synthesis of the Thienamycin Nucleus and dl-Descysteaminylthienamycin. J Am Chem Soc. 1978;100(25):8006-7.
Chambers, et al., Imipenem for treatment of tuberculosis in mice and humans. Antimicrobial Agents Chemother. Jul. 2005 ; 49(7): 2816-2821.
Charnas, et al., Chemical studies on the inactivation of *Escherichia coli* RTEM beta-lactamase by clavulanic acid. Biochemistry. May 30, 1978;17(11):2185-9.
Chen et al., MolProbity: all-atom structure validation for macromolecular crystallography. Acta Crystallogr D Biol Crystallogr. Jan. 2010;66(Pt 1):12-21.

(Continued)

*Primary Examiner* — Joseph R Kosack
*Assistant Examiner* — Sagar Patel
(74) *Attorney, Agent, or Firm* — Casimir Jones, S.C.; Jeffrey W. Childers

(57) ABSTRACT

Antibacterial agents against D,D- and L,D-transpeptidases are disclosed. Pharmaceutical compositions and methods of using the same also are disclosed.

15 Claims, 22 Drawing Sheets
(15 of 22 Drawing Sheet(s) Filed in Color)

(56) References Cited

OTHER PUBLICATIONS

Collaborative Computational Project, No. 4, The CCP4 suite: programs for protein crystallography. Acta Crystallogr D Biol Crystallogr. Sep. 1, 1994;50(Pt 5):760-3.

Cordillot, et al., In vitro cross-linking of *Mycobacterium tuberculosis* peptidoglycan by L,D-transpeptidases and inactivation of these enzymes by carbapenems. Antimicrob Agents Chemother. Dec. 2013;57(12):5940-5.

Correale et al., Structures of free and inhibited forms of the L,D-transpeptidase LdtMt1 from *Mycobacterium tuberculosis*. Acta Crystallogr D Biol Crystallogr. Sep. 2013;69(Pt 9):1697-706.

De Lorenzo et al., Efficacy and safety of meropenem-clavulanate added to linezolid-containing regimens in the treatment of MDR-/XDR-TB. Eur Respir J. Jun. 2013;41(6):1386-92.

Dhar et al., Rapid cytolysis of *Mycobacterium tuberculosis* by faropenem, an orally bioavailable β-lactam antibiotic. Antimicrob Agents Chemother. Feb. 2015;59(2):1308-19.

Diacon et al., β-Lactams against Tuberculosis—New Trick for an Old Dog? N. Engl J Med. Jul. 28, 2016;375(4):393-4.

Drawz et al., Inhibition of the class C beta-lactamase from *Acinetobacter* spp.: insights into effective inhibitor design. Biochemistry. Jan. 19, 2010;49(2):329-40.

Ekins et al., Enhancing hit identification in *Mycobacterium tuberculosis* drug discovery using validated dual-event Bayesian models. PLoS One. May 7, 2013;8(5):e63240.

Emsley et al., Coot: model-building tools for molecular graphics. Acta Crystallogr D Biol Crystallogr. Dec. 2004;60(Pt 12 Pt 1):2126-32.

England et al., Meropenem-clavulanic acid shows activity against *Mycobacterium tuberculosis* in vivo. Antimicrob Agents Chemother. Jun. 2012;56(6):3384-7.

Erdemli et al., Targeting the cell wall of *Mycobacterium tuberculosis*: structure and mechanism of L,D-transpeptidase 2. Structure. Dec. 5, 2012;20(12):2103-15.

Ernest et al., The Penems, a New Class of β-lactam antibiotics: 6-acylaminopenem-3-carboxylic acids. J. Am. Chem. Soc., 1978;100(26):8214-22.

Evans et al., A General Method for the Synthesis of Enantiomerically Pure b-Substituted, b-Amino Acids through a-Substituted Succinic Acid Derivatives. J Org Chem. 1999; 64(17): 6411-6417.

Freeman et al., Four enzymes define the incorporation of coenzyme A in thienamycin biosynthesis. PNAS. Aug. 2008;105(32):11128-11133.

Fung-Tomc et al., Structure-activity relationships of carbapenems that determine their dependence on porin protein D2 for activity against Pseudomonas aeruginosa. Antimicrob Agents Chemother. Feb. 1995;39(2):394-9.

Gavan et al., A microdilution method for antibiotic susceptibility testing: an evaluation. Am J Clin Pathol. Jun. 1970;53(6):880-5.

Gupta et al., The *Mycobacterium tuberculosis* protein LdtMt2 is a nonclassical transpeptidase required for virulence and resistance to amoxicillin. Nat Med. Apr. 2010;16(4):466-9.

Hamad, The antibiotics market. Nat Rev Drug Discov. Sep. 2010;9(9):675-6.

Hikida et al., Inactivation of new carbapenem antibiotics by dehydropeptidase-I from porcine and human renal cortex. J Antimicrob Chemother. Aug. 1992;30(2):129-34.

Horita et al., In vitro susceptibility of *Mycobacterium tuberculosis* isolates to an oral carbapenem alone or in combination with β-lactamase inhibitors. Antimicrob Agents Chemother. Nov. 2014;58(11):7010-4.

Hugonnet et al., Meropenem-clavulanate is effective against extensively drug-resistant *Mycobacterium tuberculosis*. Science. Feb. 27, 2009;323(5918):1215-8.

Isoda et al., A Practical and Facile Synthesis of Azetidine Derivatives for Oral Carbapenem, L-084. Chem Pharm Bull (Tokyo). Oct. 2006;54(10):1408-11.

Kaushik et al., Carbapenems and Rifampin Exhibit Synergy against *Mycobacterium tuberculosis* and *Mycobacterium abscessus*. Antimicrob Agents Chemother. Oct. 2015;59(10):6561-7.

Kim et al., Structural basis for the inhibition of *Mycobacterium tuberculosis* L,D-transpeptidase by meropenem, a drug effective against extensively drug-resistant strains. Acta Crystallogr D Biol Crystallogr. Mar. 2013;69(Pt 3):420-31.

Kumar et al., Meropenem inhibits D,D-carboxypeptidase activity in Mycobacterium tuberculosis. Mol Microbiol. Oct. 2012;86(2):367-81.

Kumar et al., Non-classical transpeptidases yield insight into new antibacterials. Nat Chem Biol. Jan. 2017;13(1):54-61.

Kumura et al., Synthesis and antibacterial activity of novel lincomycin derivatives. I. Enhancement of antibacterial activities by introduction of substituted azetidines. J Antibiot (Tokyo). Jun. 2016;69(6):440-5.

Lancaster, et al., Efficient Synthesis of Thietanes and Thiete 1,1-Dioxide using Phase-Transfer Catalysis. Synthesis. 1982; 1982(7): 582-583.

Lavollay et al., The peptidoglycan of stationary-phase *Mycobacterium tuberculosis* predominantly contains cross-links generated by L,D-transpeptidation. J Bacteriol. Jun. 2008;190(12):4360-6.

Lecoq et al., Dynamics Induced by β-Lactam Antibiotics in the Active Site of Bacillus subtilisl,d-Transpeptidase. Structure. May 9, 2012;20(5):850-61.

Lee et al., A 1.2-A snapshot of the final step of bacterial cell wall biosynthesis. Proc Natl Acad Sci U S A. Feb. 13, 2001;98(4):1427-31.

Li et al., Crystal structure of L,D-transpeptidase LdtMt2 in complex with meropenem reveals the mechanism of carbapenem against *Mycobacterium tuberculosis*. Cell Res. May 2013;23(5):728-31.

Maddry et al., Antituberculosis activity of the molecular libraries screening center network library. Tuberculosis (Edinb). Sep. 2009;89(5):354-63.

Mainardi et al., A novel peptidoglycan cross-linking enzyme for a beta-lactam-resistant transpeptidation pathway. J Biol Chem. Nov. 18, 2005;280(46):38146-52.

Mainardi et al., Unexpected Inhibition of Peptidoglycan LD-transpeptidase From Enterococcus Faecium by the Beta-Lactam Imipenem. J Biol Chem. Oct. 19, 2007;282(42):30414-22.

McCoy, Solving structures of protein complexes by molecular replacement with Phaser. Acta Crystallogr D Biol Crystallogr. Jan. 2007;63(Pt 1):32-41.

Meroueh et al., Structural aspects for evolution of beta-lactamases from penicillin-binding proteins. J Am Chem Soc. Aug. 13, 2003;125(32):9612-8.

Minor et al., HKL-3000: the integration of data reduction and structure solution—from diffraction images to an initial model in minutes. Acta Crystallogr D Biol Crystallogr. Aug. 2006;62(Pt 8):859-66.

Murshdov et al., REFMAC5 for the refinement of macromolecular crystal structures. Acta Crystallogr D Biol Crystallogr. Apr. 2011;67(Pt 4):355-6.

Nitanai, et al., Crystal Structure of Human Renal Dipeptidase Involved in β-Lactam Hydrolysis. J Mol Biol. Aug. 9, 2002;321(2):177-84.

Palmero et al., First series of patients with XDR and pre-XDR TB treated with regimens that included meropenen-clavulanate in Argentina. Arch Bronconeumol. Oct. 2015;51(10):e49-52.

Payen et al., Clinical use of the meropenem-clavulanate combination for extensively drug-resistant tuberculosis. Int J Tuberc Lung Dis. Apr. 2012;16(4):558-60.

Pfaendler, et al., Structure, Reactivity, and Biological Activity of Strained Bicyclic β-Lactams. J Am Chem Soc. 1981;103(15):4526-4531.

Reynolds et al., High throughput screening of a library based on kinase inhibitor scaffolds against *Mycobacterium tuberculosis* H37Rv. Tuberculosis (Edinb). Jan. 2012;92(1):72-83.

Rotilie et al., Microdilution technique for antimicrobial susceptibility testing of anaerobic bacteria. Antimicrob Agents Chemother. Mar. 1975;7(3):311-15.

Rullas et al., Combinations of β-Lactam Antibiotics Currently in Clinical Trials Are Efficacious in a DHP-I-Deficient Mouse Model of Tuberculosis Infection. Antimicrob Agents Chem other. Aug. 2015;59(8):4997-9.

(56) References Cited

OTHER PUBLICATIONS

Sanders et al., Phenotypic analysis of *Eschericia coli* mutants lacking L,D-transpeptidases. Microbiology. Sep. 2013;159(Pt 9):1842-52.

Schoonmaker et al., Nonclassical transpeptidases of *Mycobacterium tuberculosis* alter cell size, morphology, the cytosolic matrix, protein localization, virulence, and resistance to β-lactams. J Bacteriol. Apr. 2014;196(7):1394-402.

Seki et al., Effcient synthesis of 1β-methylcarbapenems based on the counter-attack strategy. J. Chem. Soc., Perkin Trans., 1996, 1:2851-6.

Silva et al., Targeting the cell wall of *Mycobacterium tuberculosis*: a molecular modeling investigation of the interaction of imipenem and meropenem with L,D-transpeptidase 2. J Biomol Struct Dyn. 2016;34(2):304-17.

Singh et al., Design, Synthesis, Structure—Function Relationship, Bioconversion, and Pharmacokinetic Evaluation of Ertapenem Prodrugs. J Med Chem. Oct. 23, 2014;57(20):8421-44.

Sugimura et al., Research on New Beta-Lactam Antibiotics; Penem and Carbapenem. Yakugaku Zasshi. Mar. 1987;107(3):175-91.

Terwilliger et al., Iterative model building, structure refinement and density modification with the PHENIX AutoBuild wizard. Acta Crystallogr D Biol Crystallogr. Jan. 2008;64(Pt 1):61-9.

Triboulet et al., Inactivation kinetics of a new target of beta-lactam antibiotics. J Biol Chem. Jul. 1, 2011;286(26):22777-84.

Veziris et al., Activity of carbapenems combined with clavulanate against murine tuberculosis. Antimicrob Agents Chemother. Jun. 2011;55(6):2597-600.

Volkmann et al., 2-Thioalkyl Penems: An Efficient Synthesis of Sulopenem, a (5R, 6S)-6-(1(R )-Hydroxyethyl)-2-[(cis-1-oxo-3-thiolanyl)thio]-2-penem Antibacterial. J Org Chem. 1992;57(16):4352-4361.

Wivagg et al., Mechanisms of β-lactam killing and resistance in the context of *Mycobacterium tuberculosis*. J Antibiot (Tokyo). Sep. 2014;67(9):645-54.

Zwart et al., Automated structure solution with the PHENIX suite. Methods Mol Biol. 2008;426:419-35.

International Search Report and Written Opinion for PCT/US2017/055828, dated Nov. 29, 2017, 15 pages.

EP Partial Search Report for EP 1785990.8, dated Mar. 13, 2020, 14 pages.

Dubee et al., Inactivation of *Mycobacterium tuberculosis* I,d-transpeptidase LdtMt$_1$ by carbapenems and cephalosporins. Antimicrob Agents Chemother. Aug. 2012;56(8):4189-95.

Nishimura et al., Structural comparison of 1 beta-methylcarbapenem, carbapenem and penem: NMR studies and theoretical calculations. Bioorg Med Chem. Apr. 1998;6(4):367-75.

Sunagawa et al., New penem compounds with 5'-substituted pyrrolidinylthio group as a C-2 side chain; comparison of their biological properties with those of carbapenem compounds. J Antibiot (Tokyo). Apr. 1992;45(4):500-4.

EP Extended Search Report for EP 1785990.8, dated Jun. 18, 2020, 19 pages.

\* cited by examiner

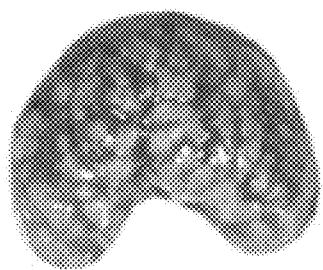  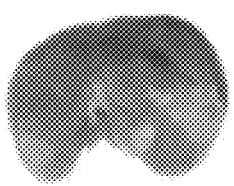 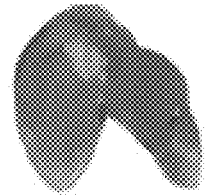
FIG. 1D   FIG. 1E   FIG. 1F   FIG. 1G
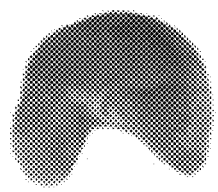 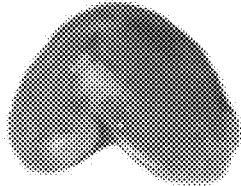 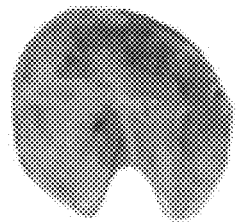 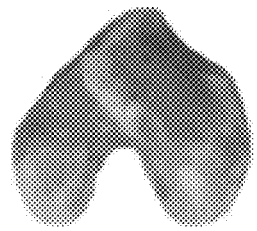
FIG. 1H   FIG. 1I   FIG. 1J   FIG. 1K

FIG. 6

| Enzyme | Molecular weight (Da) of adducts formed with the following β-lactams | | | | | | | | | |
|---|---|---|---|---|---|---|---|---|---|---|
| | Amoxicillin | Cephalothin | Doripenem | Faropenem | A-C-Z-F | D-B-F-Te | T205 | T206 | T208 | T210 |
| Ldt$_{Mt1}$ | No adduct | No adduct | +376, +421 | +86 | +86 | +86 | +316 | +344 | +385 | +258 |
| Ldt$_{Mt2}$ | No adduct | +335 | +123 | +86 | +86 | +86 | +337 | +344 | +383 | +257 |
| Ldt$_{Mab1}$ | +366 | +337, +355 | +376, +421 | +86 | +86 | +86 | +337 | +344 | +383 | +258 |
| Ldt$_{Mab2}$ | No adduct | No adduct | +68 | +86 | +86 | +86 | No adduct | No adduct | No adduct | No adduct |
| Ldt$_{Kp}$ | No adduct | No adduct | +376, +421 | +86, +288 | +86 | +86 | +317 | +344 | No adduct | +258 |
| Ldt$_{Cl}$ | No adduct | +337 | +376, +421 | +86, +172 | +86 | +86 | +316 | +344 | +383 | +258 |
| Ldt$_{Pa}$ | No adduct | No adduct | No adduct | +86, +288 | +457 | n.d. | +317 | No adduct | +56 | +258 |

ANTIBACTERIAL AGENTS AGAINST D,D- AND L,D-TRANSPEPTIDASES

CROSS-REFERENCE TO RELATED APPLICATIONS

This application claims the benefit of U.S. Provisional Application No. 62/406,095 filed Oct. 10, 2016, the contents of which are incorporated herein by reference in its entirety.

FEDERALLY SPONSORED RESEARCH OR DEVELOPMENT

This invention was made with government support under AI121072 and AI014937 awarded by the National Institutes of Health. The government has certain rights in the invention.

BACKGROUND

Decades-old drugs comprise the standard regimens available today for the treatment of tuberculosis (TB), a disease caused by infection with *Mycobacterium tuberculosis*. Despite being declared a global health priority by the World Health Organization more than twenty years ago, TB currently causes more deaths worldwide than any other infectious disease (WHO, 2015). The complexity and length of TB treatment, involving the daily administration of multiple drugs for at least six months, precludes its successful implementation in many regions of the world. This failure fuels the development of drug-resistant TB, further exacerbating this already serious global public health problem. Drug regimens that can reduce the complexity and duration of treatment and that also have activity against drug-resistant *M. tuberculosis* could significantly impact the control of TB and alleviate the suffering of patients with this disease. The development of new anti-TB drugs, including the repurposing and/or improvement of existing drugs, is thus of critical importance.

The β-lactam antibacterials, which target peptidoglycan biosynthesis and are overall the most widely utilized class of antibacterials for the treatment of infections, have traditionally not been effective in TB treatment (Walsh, 2003). This lack of activity against *M. tuberculosis* has primarily been attributed to the presence of the chromosomally-encoded β-lactamase enzyme BlaC, which hydrolyzes the core β-lactam ring to deactivate the drug (Hugonnet, et al., 2009) and also to the potential for limiting penetration of the thick mycolate coat (Wivagg, et al., 2014). However, recently a number of studies have suggested that a subset of β-lactams, specifically the carbapenems, as well as the penem faropenem, may have anti-TB activity (Cordillot, et al., 2013; Dhar, et al., 2015; Kaushik, et al., 2015; Rullas, et al., 2015). In addition to being relatively more resistant to β-lactamase activity, these types of β-lactams are unique in that they target more than one enzyme involved in bacterial peptidoglycan synthesis.

Most β-lactams inhibit D,D-transpeptidases, commonly known as penicillin-binding proteins. These enzymes catalyze the formation of 4→3 transpeptide linkages in the peptidoglycan network. Emerging evidence suggests that carbapenems target not only the D,D-transpeptidases, but also the non-canonical L,D-transpeptidases, which catalyze the formation of 3→3 transpeptide linkages (Cordillot, et al., 2013; Gupta, et al., 2010; Erdemli, et al., 2012). This latter function may be key to the anti-TB activity observed with faropenem and carbapenems as *M. tuberculosis* primarily uses L,D-transpeptidases to cross-link its peptidoglycan (Lavollay, et al., 2008; Kumar, et al., 2012) and mutants lacking the L,D-transpeptidases $Ldt_{Mt1}$ and $Ldt_{Mt2}$ are attenuated in virulence, have modified peptidoglycan, and altered cell physiology and morphology (Gupta, et al., 2010; Schoonmaker, et al., 2014). A better understanding of how these types of β-lactam antibacterials act against *M. tuberculosis* may therefore lead to structural improvements for their use as anti-TB drugs.

SUMMARY

The presently disclosed subject matter provides novel lactam antibacterial agents that contain a bicyclic penem core bearing substituents at the C-2 and C-6 positions. Kinetics and x-ray structural studies verified that the presently disclosed compounds bind to L,D-transpeptidases (enzymes involved in the biosynthesis of the peptidoglycan layer that are distinct from classical D,D-transpeptidases) of several bacterial pathogens important to human health. Such pathogens include Gram-positive, Gram-negative and acid-fast bacteria. The presently disclosed compounds exhibit potent antimicrobial activity.

In some aspects, the presently disclosed subject matter provides compounds of formula (I):

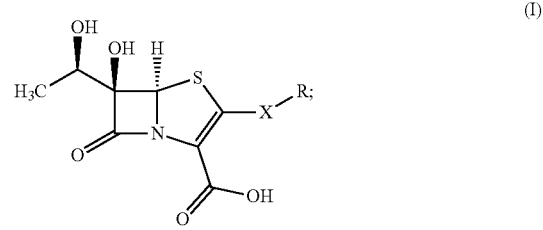

wherein:
X is selected from the group consisting of CR'R" and S;
R' and R" are each independently selected from the group consisting of hydrogen, and $C_1$-$C_6$ alkyl;
R is selected from the group consisting of:

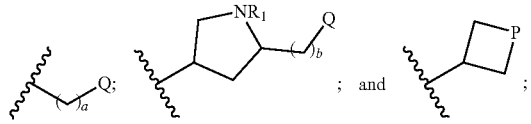

a is an integer selected from the group consisting of 0, 1, 2, 3, 4, 5 and 6; b is an integer selected from the group consisting of 0, 1, 2, and 3; $R_1$ is selected from the group consisting of hydrogen, and $C_1$-$C_6$ alkyl; Q is selected from the group consisting of hydrogen, hydroxyl, alkoxyl, amine, carbonyl, carboxyl, ester, ether, thiol, sulfide, sulfinyl, sulfonyl, and heterocycloalkyl;
P is selected from the group consisting of amine, sulfide, sulfonyl, and sulfinyl; and stereoisomers and pharmaceutically acceptable salts thereof.

In certain aspects, the presently disclosed subject matter provides a method of treating a bacterial infection comprising administering a therapeutically effective amount of the compound of formula (I) to a subject in need thereof.

In other aspects, the presently disclosed subject matter provides a pharmaceutical composition comprising a compound of formula (I) and one or more additional ingredients.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

Figure 3A:
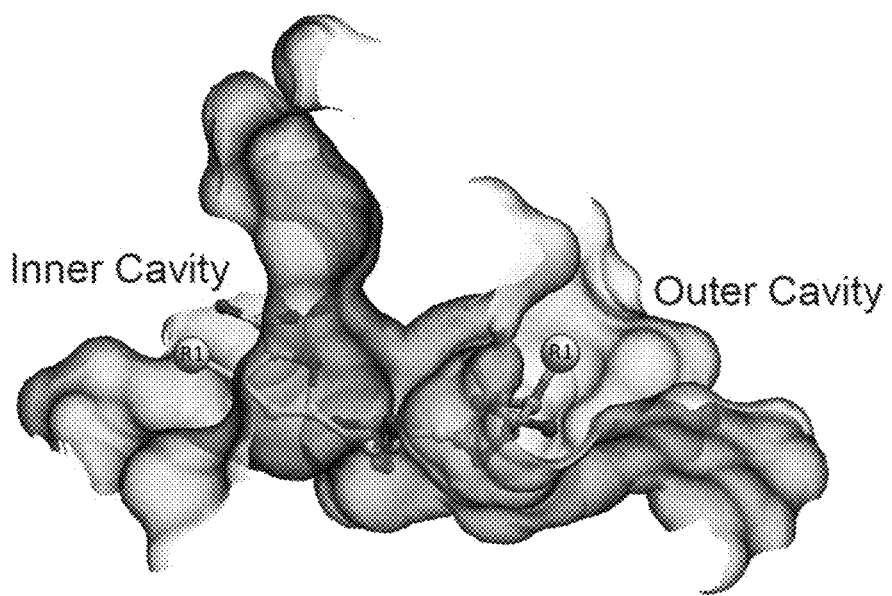
Figure 3B:
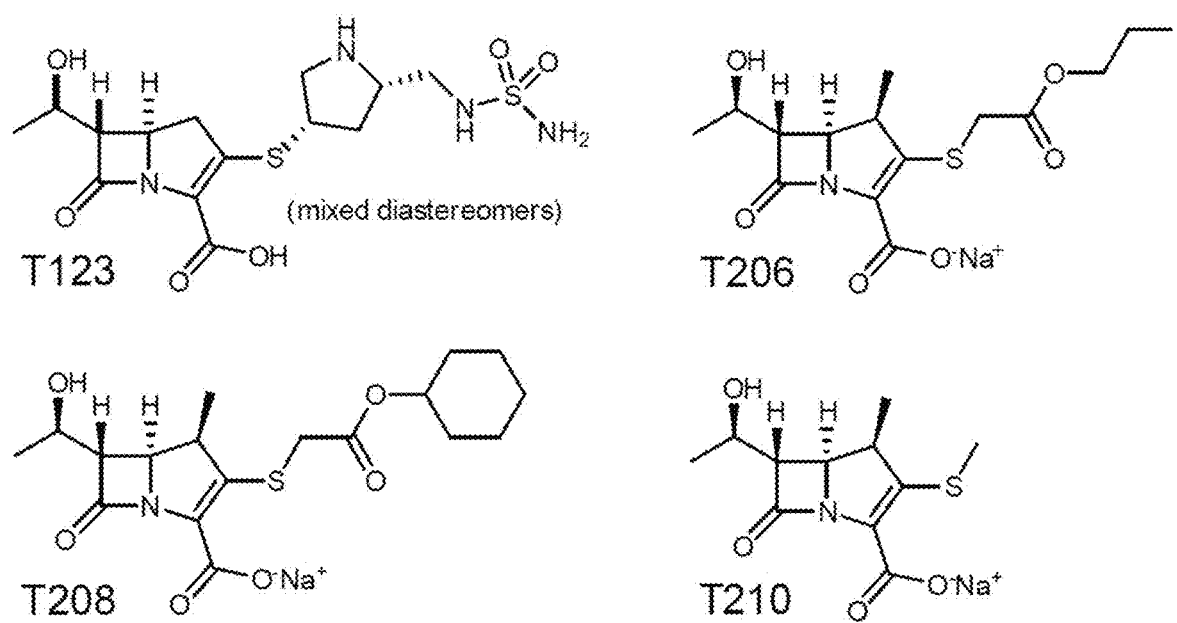
Figure 3C:
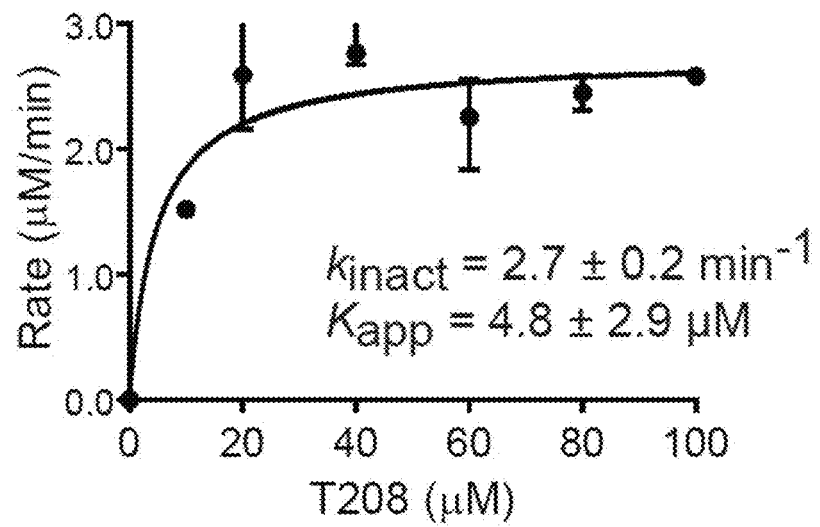
Figure 3C:
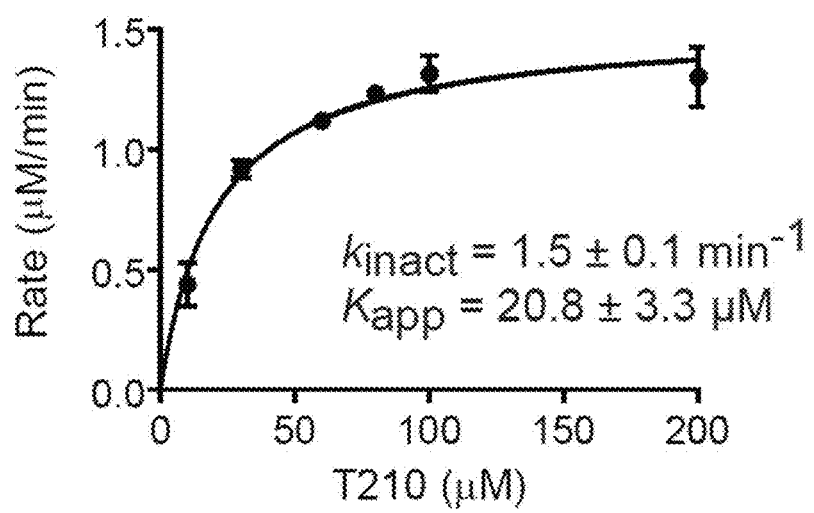
Figure 5A:
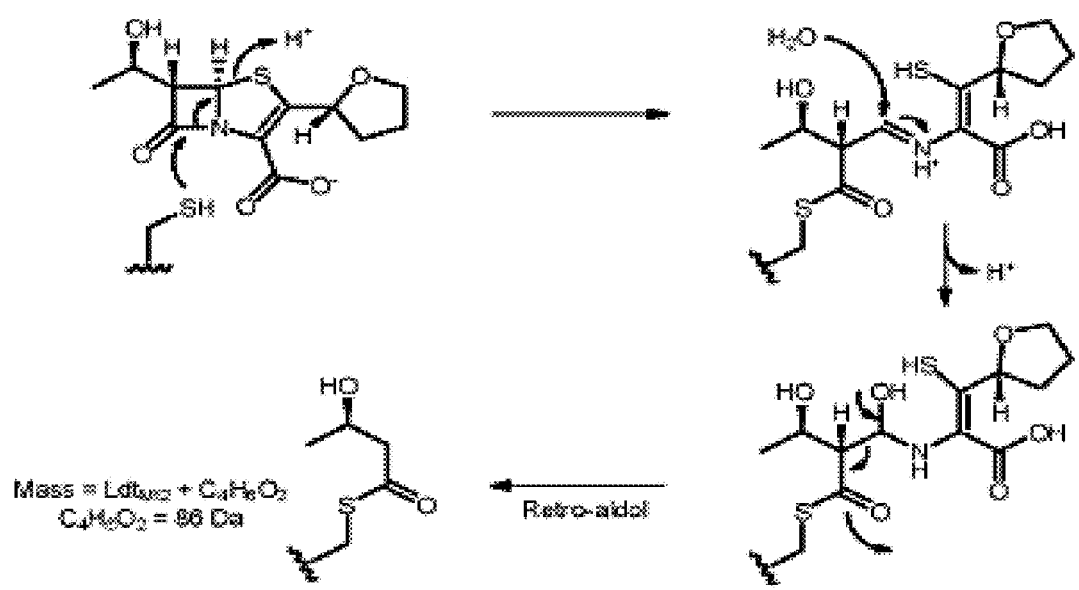
Figure 5B:
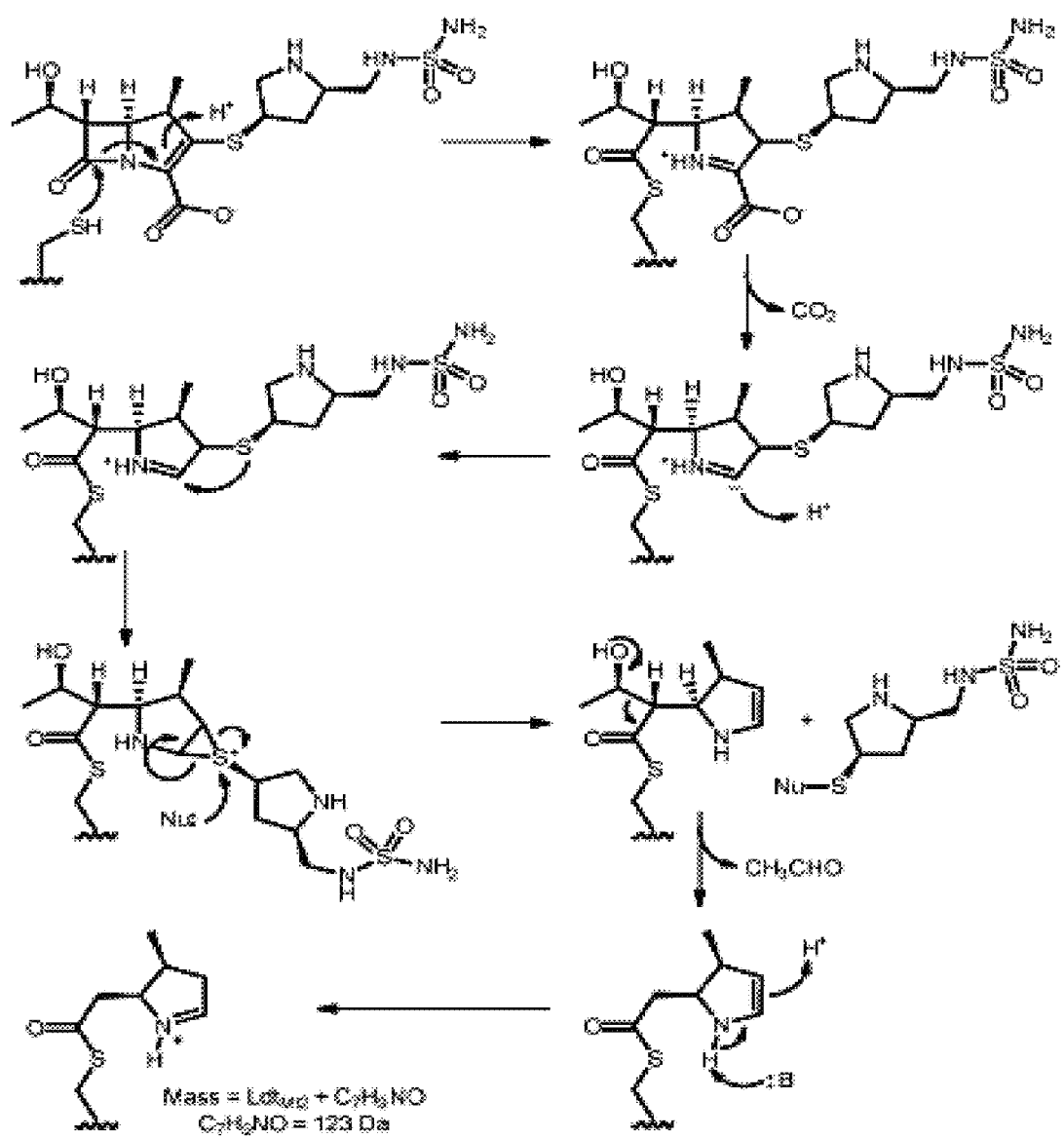
Figure 5C:
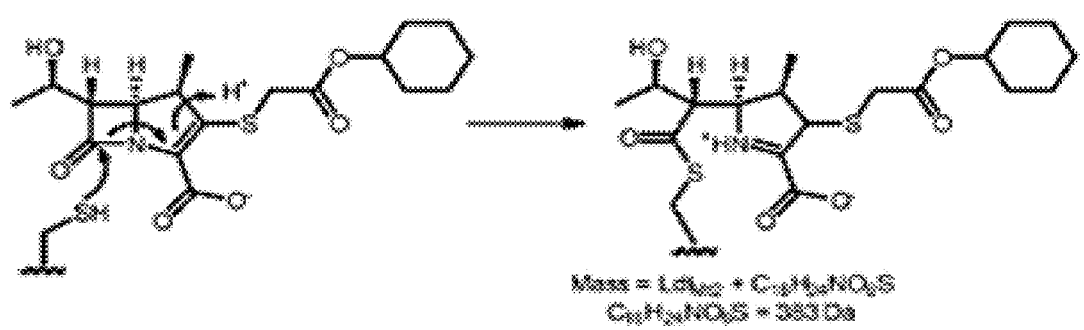

Having thus described the presently disclosed subject matter in general terms, reference will now be made to the accompanying Figures, which are not necessarily drawn to scale, and wherein:

FIG. 1A, FIG. 1B, FIG. 1C, FIG. 1D, FIG. 1E, FIG. 1F, FIG. 1G, FIG. 1H, FIG. 1I, FIG. 1J, and FIG. 1K show the interactions of β-lactams with mycobacterial L,D-transpeptidases and activity of biapenem and faropenem in the mouse model of TB: (FIG. 1A) binding of faropenem to *M. tuberculosis* enzymes $Ldt_{Mt1}$ and $Ldt_{Mt2}$, and *M. abscessus* enzymes $Ldt_{Mab1}$ and $Ldt_{Mab2}$. In each panel, the top plot displays the titration of faropenem to enzyme and the bottom panel displays the non-linear fit of heat exchange across increasing ligand: enzyme molar ratios; (FIG. 1B) nitrocefin hydrolyzing activity of $Ldt_{Mt2}$ following incubation with various β-lactams; (FIG. 1C) $Log_{10}$ colony forming units of *M. tuberculosis* in the lungs of BALB/c mice before, during and after treatment with biapenem and faropenem alone or in combination with rifampin and control regimens. Data represent the mean (n=5 mice per group per time point) and error bars represent the standard deviation; (FIG. 1D, FIG. 1E, FIG. 1F, FIG. 1G, FIG. 1H, FIG. 1I, FIG. 1J, and FIG. 1K) are the gross pathology of lungs of *M. tuberculosis*-infected mice at the end of treatment. One representative lung from each treatment group is shown: (FIG. 1D) no treatment, (FIG. 1E) isoniazid, (FIG. 1F) rifampin, (FIG. 1G) isoniazid+rifampin, (FIG. 1H) biapenem, (FIG. 1I) biapenem+rifampin, (FIG. 1J) faropenem, (FIG. 1K) faropenem+rifampin. Scale bar, 1 cm;

FIG. 2A, FIG. 2B, FIG. 2C, and FIG. 2D show molecular details of interactions of *M. tuberculosis* L,D-transpeptidases with (carba)penems: (FIG. 2A) crystal structures of $Ldt_{Mt2}$ bound by faropenem at 2.17 Å; (FIG. 2B) $Ldt_{Mt1}$ bound by faropenem at 2.25 Å; and (FIG. 2C) $Ldt_{Mt2}$ bound by doripenem at 2.18 Å. Residues that make significant interactions are shown in green and adducts are shown in cyan. The 2Fo-2Fc difference Fourier map (gray) is contoured at 1.0σ. Distances are in Å; and (FIG. 2D) kinetics of inhibition of $Ldt_{Mt2}$ by doripenem, biapenem, faropenem and tebipenem. Kinetic constants $k_{inact}$ and $K_{app}$ were determined spectrophotometrically. Data represent the mean of three independent experiments and error bars represent standard deviation;

FIG. 3A, FIG. 3B, and FIG. 3C show the design and activity of evolved carbapenems: (FIG. 3A) model of carbapenem bound to the catalytic core of $Ldt_{Mt2}$. While the carbapenem core ring is tightly bound to the catalytic core (gray) of $Ldt_{Mt2}$ by covalent bonding to cysteine 354, its R1 group protrudes and makes extensive contacts with either the inner cavity (pocket colored purple, ligand colored beige) or the outer cavity (pocket colored yellow, ligand colored green), depending on the ligand binding mode; (FIG. 3B) chemical structures of evolved carbapenems T123, T206, T208 and T210; (FIG. 3C) kinetics of acylation of $Ldt_{Mt2}$ by T208 and T210. Kinetic constants $k_{inact}$ and $K_{app}$ were determined spectrophotometrically. Data represent the mean of three independent experiments and error bars represent standard deviation;

FIG. 4A, FIG. 4B, FIG. 4C, FIG. 4D, FIG. 4E and FIG. 4F show the crystal structures of $Ldt_{Mt2}$ with evolved carbapenems: (FIG. 4A, FIG. 4B, and FIG. 4C) Structure with T206 at the catalytic site of $Ldt_{M}t2$. (FIG. 4A) Conformation A1, (FIG. 4B) conformation A2 and (FIG. 4C) conformation B showing interactions of T206. Structure of adducts (cyan) of (FIG. 4D) T208, (FIG. 4E) T210 and (FIG. 4F) T224 at the catalytic site of $Ldt_{Mt2}$. For each panel, the 2Fo-2Fc difference Fourier map (gray) is contoured at 1.0σ. Distances are in Å;

FIG. 5A, FIG. 5B, and FIG. 5C show the proposed mechanism of acylation of L,D-transpeptidases by (carba)penems: (FIG. 5A) reaction of faropenem with $Ldt_{Mt1}$ or $Ldt_{Mt2}$, and reaction of $Ldt_{Mt2}$ with (FIG. 5B) doripenem and (FIG. 5C) T208; and FIG. 6 shows UPLC-MS analysis of adducts formed between L,D-transpeptidases and β-lactams. Molecular weights (Da) of β-lactams: amoxicillin (A), 365.4; cephalothin (C); 396.4; doripenem (D), 420.1; faropenem (F), 285.3; aztreonam (Z), 435.4; biapenem (B), 350.4; tebipenem (Te), 383.5; T205, 337.3; T206, 365.4; T208, 405.4; T210, 279.3. A-C-Z-F and D-B-F-Te represent incubation of the enzymes with equimolar mixture of the indicated β-lactams. n.d., not determined.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Antibacterial Agents Against D,D- and L,D-Transpeptidases

Bacterial survival requires an intact peptidoglycan layer, a 3-dimensional exoskeleton that encapsulates the cytoplasmic membrane. Historically, the final steps of peptidoglycan synthesis are known to be carried out by D,D-transpeptidases, enzymes that are inhibited by the β-lactams which constitute >50% of all antibacterials in clinical use. The presently disclosed subject matter demonstrates that the carbapenem subclass of β-lactams is distinctly effective, not only because they inhibit D,D-transpeptidases and are poor substrates for β-lactamases, but primarily because they also inhibit non-classical transpeptidases, namely the L,D-transpeptidases, which generate the majority of linkages in the peptidoglycan of mycobacteria. The presently disclosed subject matter, in part, elucidates the molecular mechanisms responsible for inhibition of L,D-transpeptidases of *M. tuberculosis* and a range of bacteria, including ESKAPE pathogens. This information was leveraged to design, synthesize and test simplified carbapenems exhibiting potent antibacterial activity.

More particularly, the presently disclosed subject matter characterized the inhibitory interactions using biochemical and biophysical approaches, including solving multiple crystal structures, of faropenem and carbapenems with the *M. tuberculosis* L,D-transpeptidases Ldt$_{Mt1}$ and Ldt$_{Mt2}$ and validated carbapenem anti-TB activity in vivo in a preclinical mouse model of TB treatment. Based on these data, structure-activity relationships could be analyzed and used to direct the synthesis of evolved carbapenems exhibiting potent activity against *M. tuberculosis*. In addition, putative L,D-transpeptidases from other bacteria, including ESKAPE pathogens (organisms associated with severe, difficult-to-treat nosocomial infections) were identified and the inhibitory interactions of faropenem and carbapenems, including the test series of evolved carbapenems, with these enzymes was characterized. Accordingly, the presently disclosed data not only provide critical insights into maximizing the anti-TB activity of carbapenems, but also for wider use to improve their therapeutic potential as antibacterial agents.

A. Compounds of Formula (I)

Accordingly, in some embodiments, the presently disclosed subject matter provides a compound of formula (I):

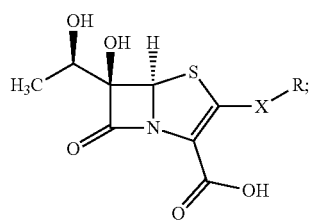

wherein:

X is selected from the group consisting of CR'R" and S;
R' and R" are each independently selected from the group consisting of hydrogen, and $C_1$-$C_6$ alkyl;
R is selected from the group consisting of:

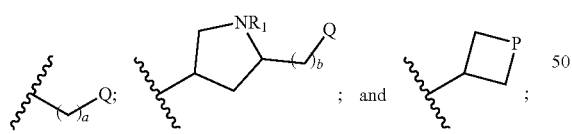

a is an integer selected from the group consisting of 1, 2, 3, 4, 5 and 6; b is an integer selected from the group consisting of 0, 1, 2, and 3; $R_1$ is selected from the group consisting of hydrogen, and $C_1$-$C_6$ alkyl; Q is selected from the group consisting of hydrogen, hydroxyl, alkoxyl, amine, carbonyl, carboxyl, ester, ether, thiol, sulfide, sulfinyl, sulfonyl, and heterocycloalkyl; and
P is selected from the group consisting of amine, sulfide, sulfonyl, and sulfinyl; and stereoisomers and pharmaceutically acceptable salts thereof.

In some embodiments, Q is selected from the group consisting of pyrrolidinyl, morpholinyl, and N-methylpiperazinyl.

In particular embodiments, Q is selected from the group consisting of H, —OR$_2$, —NR$_3$R$_4$, —C(=O)—NR$_3$R$_4$, —C(=O)—OR$_5$, and —NH—SO$_2$—NR'R"; P is selected from the group consisting of —N(R$_6$)—, and —SO$_2$—; R$_2$ is selected from the group consisting of hydrogen and $C_1$-$C_6$ alkyl, $C_6$-$C_{12}$ aryl, and $C_4$-$C_{16}$ alkylaryl; R$_3$ and R$_4$ are each independently selected from the group consisting of hydrogen, $C_1$-$C_6$ alkyl, and —SO$_2$NR$_3$R$_4$; R$_5$ is selected from the group consisting of hydrogen, and $C_1$-$C_6$ alkyl, $C_3$-$C_{12}$ cycloalkyl, $C_6$-$C_{12}$ aryl, and $C_4$-$C_{16}$ alkylaryl; R$_6$ is selected from the group consisting of

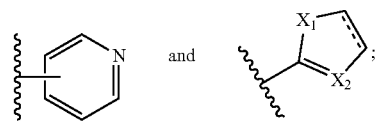

═══ represents a single or a double bond; X$_1$ and X$_2$ are each independently selected from the group consisting of C, O, N, and S.

In further embodiments, the compound of formula (I) is a compound of formula (Ia):

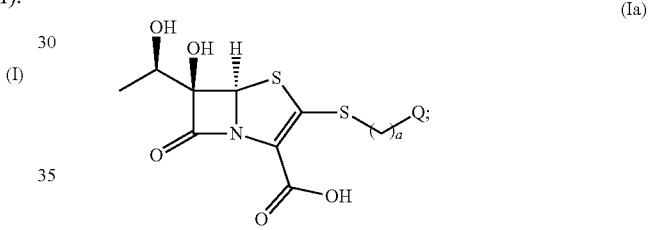

wherein: (i) Q is H; and a is 2 or 3; or (ii) Q is —OR$_2$; a is 2; and R$_2$ is H; or (iii) Q is —C(=O)—OR$_5$; a is 2; and R$_5$ is $C_1$-$C_6$ alkyl.

In certain embodiments, the compound of formula (Ia) is selected from the group consisting of:

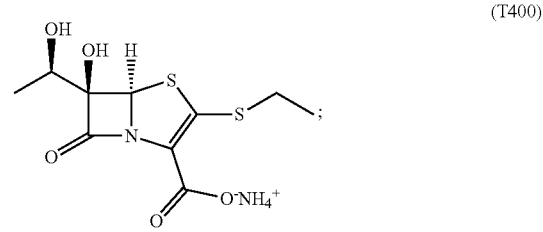

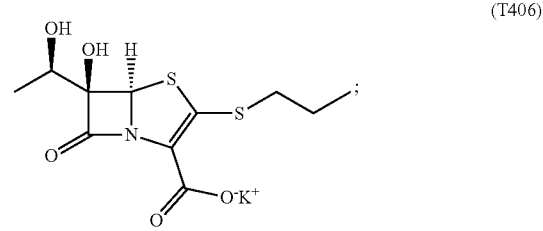

-continued

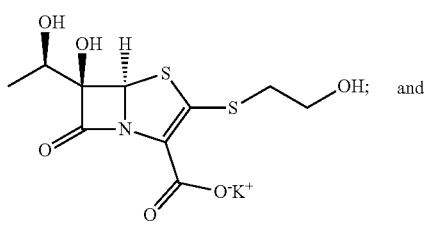
(T407)

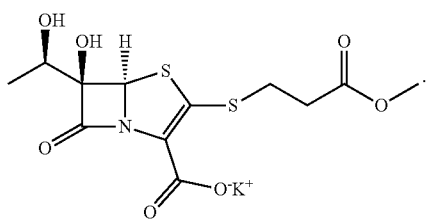
(T408)

In other embodiments, the compound of formula (I) is a compound of formula (Ib):

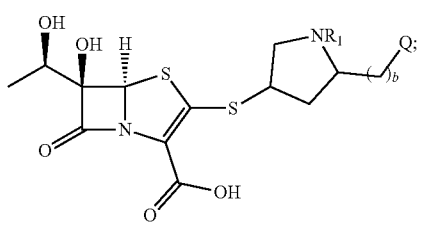
(Ib)

wherein: (i) Q is —NR$_3$R$_4$; R$_1$ is H; b is 1; R$_3$ is H; and R$_4$ is H or —SO$_2$NR$_3$R$_4$; or (ii) Q is —C(═O)—NR$_3$R$_4$; R$_1$ is H; b is 0; R$_3$ is C$_1$-C$_6$ alkyl; and R$_4$ is C$_1$-C$_6$ alkyl.

In certain embodiments, the compound of formula (Ia) is selected from the group consisting of:

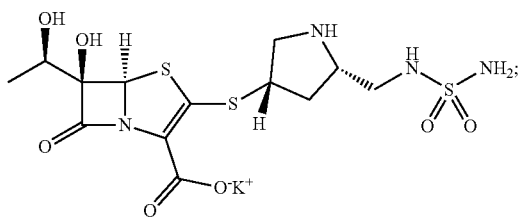
(T409)

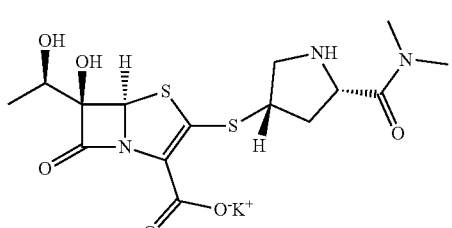
(T410)

In further embodiments, the compound of formula (I) is a compound of formula (Ic):

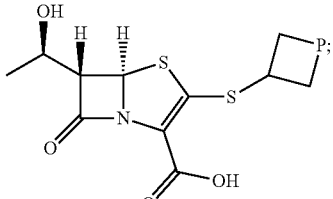
(Ic)

wherein P is —N(R$_6$)—; and R$_6$ is

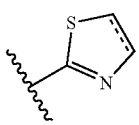

In certain embodiments, the compound of formula (Ic):

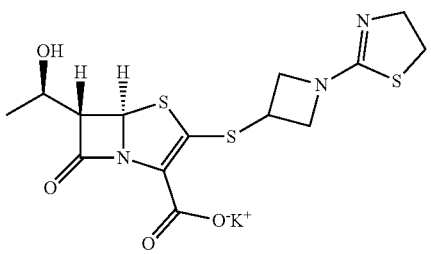
(T405)

B. Methods of Using Compounds of Formula (I)

In some embodiments, the presently disclosed subject matter provides a method of treating or preventing a bacterial infection in a subject comprising administering to the subject a therapeutically effective amount of a compound of formula (I), stereoisomer, or pharmaceutically acceptable salt thereof.

As used herein, the term "treating" can include reversing, alleviating, inhibiting the progression of, preventing or reducing the likelihood of the disease, disorder, or condition to which such term applies, or one or more symptoms or manifestations of such disease, disorder or condition, including killing or eliminating an infectious agent, such as *M. tuberculosis, M. abscessus, A. baumannii, S. aureus, K. pneumoniae, E. cloacae, P. aeruginosa* and *E. faecalis* or a combination thereof. In certain embodiments, the bacterial infection is one or more strains of bacteria that is resistant to antimicrobial agents directed to inactive D, D-transpeptidase.

Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly a compound of Formula (I) and one or more antibacterial agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compounds of Formula (I) described herein can be administered alone or in combination with adjuvants that enhance stability of the compounds of Formula (I), alone or in combination with one or more antibacterial agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compound of Formula (I) and at least one additional therapeutic agent can be varied so long as the beneficial effects of the combination of these agents are achieved. Accordingly, the phrase "in combination with" refers to the administration of a compound of Formula (I) and at least one additional therapeutic agent either simultaneously, sequentially, or a combination thereof. Therefore, a subject administered a combination of a compound of Formula (I) and at least one additional therapeutic agent can receive compound of Formula (I) and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of Formula (I) and at least one additional therapeutic agent are administered simultaneously, they can be administered to the subject as separate pharmaceutical compositions, each comprising either a compound of Formula (I) or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of Formula (I) and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

In other embodiments, the presently disclosed subject matter provides a method of inhibiting the growth of a bacteria in vitro comprising contacting the bacteria with an effective amount of a compound of formula (I), stereoisomer, or pharmaceutically acceptable salt thereof.

As used herein, the term "inhibition" or "reduction" and grammatical derivations thereof, refers to the ability of an agent to block, partially block, interfere, decrease, reduce or deactivate a biological molecule, pathway or mechanism of action. Thus, one of ordinary skill in the art would appreciate that the term "inhibit" encompasses a complete and/or partial loss of activity, e.g., a loss in activity by at least 10%, in some embodiments, a loss in activity by at least 20%, 30%, 50%, 75%, 95%, 98%, and up to and including 100%.

In some other embodiments, the presently disclosed subject matter provides a method of inhibiting L,D-transpeptidase activity in a subject with a bacterial infection, comprising administering to the subject an effective amount of a compound of formula (I), stereoisomer, or pharmaceutically acceptable salt thereof.

C. Pharmaceutical Compositions and Administration

In another aspect, the present disclosure provides a pharmaceutical composition including one compounds of formula (I), alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{25}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, 1-cyclohexenyl, 3-cyclohexenyl, cycloheptyl, and the like. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl. The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like. Other examples of heterocycloalkyl ring systems include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —CH$_2$CH$_2$CH$_2$CH$_2$—, —CH$_2$CH=CHCH$_2$—, —CH$_2$CsCCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(l-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

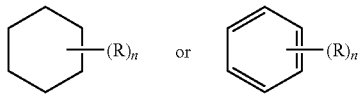

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

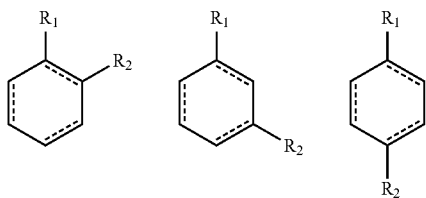

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol (  ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR"R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR"R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(═O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(═O)NR', esters, —RC(═O)OR', ketones, —RC(═O)R', and aldehydes, —RC(═O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(═O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(═O)— group. Exemplary aryloxycarbonyl groups include phenoxy- and naphthoxy-carbonyl.

"Aralkoxycarbonyl" refers to an aralkyl-O—C(═O)— group. An exemplary aralkoxycarbonyl group is benzyloxycarbonyl.

"Carbamoyl" refers to an amide group of the formula —C(═O)NH$_2$. "Alkylcarbamoyl" refers to a R'RN—C(═O)— group wherein one of R and R' is hydrogen and the other of R and R' is alkyl and/or substituted alkyl as previously described. "Dialkylcarbamoyl" refers to a R'RN—C(═O)— group wherein each of R and R' is independently alkyl and/or substituted alkyl as previously described.

The term carbonyldioxyl, as used herein, refers to a carbonate group of the formula —O—C(═O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(═O)— group, and can include an aldehyde group represented by the general formula R—C(═O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S(O$_2$)R.

The term "sulfoxide" refers to a compound having a sulfinyl group —S(O)R

The term ureido refers to a urea group of the formula —NH—CO—NH$_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Overview

Novel β-lactam antibacterials have been developed that contain a bicyclic penem core bearing substituents at C-2 and C-6. Using kinetics and x-ray structural studies, it was verified that these compounds bind to L,D-transpeptidases (enzymes involved in the biosynthesis of the peptidoglycan layer that are distinct from classical D,D-transpeptidases) of several bacterial pathogens important to human health. The pathogens include Gram-positive, Gram-negative and acid-fast bacteria. Potent antimicrobial activity has been observed.

The presently disclosed subject matter provides synthetic small molecules whose structures are recognized by the active sites of L,D-transpeptidases, and in many instances D,D-transpeptidases as well, to compete with the normal cellular substrates involved in bacterial cell wall biosynthesis and inactivate these key cell wall cross-linking enzymes. The chemical properties of the inhibitor molecules are such that they react with the catalytic amino acid residues of the transpeptidases to acylate them and, thereby, inactivate them. As a consequence of this reaction, some involving further molecular cleavages and rearrangements, all or part of the original molecule remains covalently bound to the enzyme and blocks its function and inhibit bacterial growth.

A series of penems that are active against a range of bacterial pathogens important to human health has been developed. Therefore, these potently active compositions of matter have a high potential to be licensed for commercial development into antibiotics to treat bacterial infections in humans (and animals).

Example 2

Material and Methods

The following molecules were developed for the Taskforce to study Resistance Emergence & Antimicrobial development Technology (TREAT). Their chemical description and antimicrobial properties are described below.

Antimicrobial Activity.

The standard broth dilution assay that is most widely used to determine Minimum Inhibitory Concentration (MIC) of a compound was used, which is recommended by the Clinical and Laboratory Standards Institute (Gavan, et al., 1970; Rotilie, et al., 1975; Desmond, 2011). In this method, an axenic culture of a bacterial strain is grown to a defined growth phase in the appropriate culture broth. This primary culture is used to prepare a suspension with $10^6$ live bacilli or colony forming units per mL. Simultaneously, in a sterile 96-well plate, 100 μL of culture broth and a test compound are added in such a way that consecutive wells (across a row or column) contain 2 fold dilutions of the test compound. Next, 100 μL of the bacterial suspension is added to each well, the plate is incubated under appropriate conditions and growth or lack thereof is assessed at a defined time point. For *M. tuberculosis* the end point reading was taken at 2 weeks. For *M. abscessus* the end point reading was taken at 3 days, and for the rest of the pathogens the end point reading was obtained after overnight incubation according to the Clinical and Laboratory Standards Institute recommendations (Desmond, 2011). The lowest concentration at which bacterial growth is inhibited is reported as the MIC of the compound. See Table 1.

TABLE 1

Structures of penems and summaries antimicrobial MIC90 data.

| Compound Name | Chemical Structure & Description | Antimicrobial Activities (stated as pathogen: MIC) |
|---|---|---|
| T400 | Molecular formula: $C_{10}H_{16}N_2O_4S_2$<br>Molecular weight: 292.37 | *Mycobacterium tuberculosis*: 16-32 μg/mL<br>Methicillin Resistant *Staphylococcus aureus*: 0.5-1 μg/mL<br>Methicillin Susceptible *Staphylococcus aureus*: 0.5-1 μg/mL<br>*Klebsiella pneumoniae*: 1-2 μg/mL<br>*Enterobacter cloacae*: 16-32 μg/mL |
| T405 | Molecular formula: $C_{14}H_{16}N_3O_4S_3K$<br>Molecular weight: 425.58 | *Mycobacterium tuberculosis*: 0.5-1 μg/mL<br>Methicillin Resistant *Staphylococcus aureus*: 0.03-0.06 μg/mL<br>Methicillin Susceptible *Staphylococcus aureus*: 0.03-0.06 μg/mL<br>*Klebsiella pneumoniae*: 0.125-0.25 μg/mL<br>*Enterobacter cloacae*: 0.25-0.5 μg/mL<br>*Pseudomonas aeruginosa*: 4-8 μg/mL<br>*Actinobacter baumannii* 6 M-1b: 4-8 μg/mL |
| T406 | Molecular formula: $C_{11}H_{14}NO_4S_2K$<br>Molecular weight: 327.45 | *Mycobacterium tuberculosis*: 0.5-1 μg/mL<br>*Klebsiella pneumoniae*: 0.25-0.5 μg/mL<br>*Enterobacter cloacae*: 4-8 μg/mL<br>*Actinobacter baumannii* 6 M-1b: 4-8 μg/mL |
| T407 | Molecular formula: $C_{10}H_{12}NO_5S_2K$<br>Molecular weight: 329.43 | *Mycobacterium tuberculosis*: 2-4 μg/mL<br>*Klebsiella pneumoniae*: 8-16 μg/mL |
| T408 | Molecular formula: $C_{12}H_{14}NO_6S_2K$<br>Molecular weight: 371.46 | *Mycobacterium tuberculosis*: 0.5-1 μg/mL<br>*Klebsiella pneumoniae*: 8-16 μg/mL<br>*Enterobacter cloacae*: 4-8 g/mL<br>*Actinobacter baumannii* 6 M-1b: 16-32 μg/mL |

TABLE 1-continued

Structures of penems and summaries antimicrobial MIC90 data.

| Compound Name | Chemical Structure & Description | Antimicrobial Activities (stated as pathogen: MIC) |
|---|---|---|
| T409 | Molecular formula: $C_{13}H_{19}N_4O_6S_3K$<br>Molecular weight: 462.60 | *Mycobacterium tuberculosis*: 0.5-1 µg/mL |
| T410 | Molecular formula: $C_{15}H_{20}N_3O_3S_2K$<br>Molecular weight: 425.56 | *Mycobacterium tuberculosis*: 8-16 µg/mL<br>*Klebsiella pneumoniae*: 2-4 µg/mL<br>*Enterobacter cloacae*: 1-2 µg/mL<br>*Pseudomonas aeruginosa*: 0.5-1 µg/mL<br>*Actinobacter baumannii* 6 M-1b: 0.5-1 µg/mL |

UPLC-HRMS Analysis of L,D-Transpeptidase (Ldt)/Penem Adducts:

Penems were incubated with Ldts at 4 mM concentration with 2 µM in 400 µL of 25 mM Tris, pH 8, for 5 h at room temperature, quenched with 8 µL of freshly prepared 5% TFA and filtered through a 0.2 µm sterile membrane. 3 µL of each sample was injected into a Waters Aquity H-Class UPLC system equipped with a multi-wavelength ultraviolet-visible diode array detector in conjunction with a Waters Aquity BEH-300 UPLC column packed with a C4 stationary phase (2.1×50 mm, 1.7 µm) in tandem with HRMS analysis by a Waters Xevo-G2 Q-ToF ESI mass spectrometer. Solvent A=0.1% formic acid in water, solvent B=0.1% formic acid in acetonitrile. Mobile phase (A:B)=0-1 min (90:10), 1-7.5 min (20:80), 7.5-8.4 min (20:80), 8.4-8.5 min (90:10), 8.5-10 min (90:10). Flow rate=0.3 mL min$^{-1}$. T=60° C. See Table 2.

TABLE 2

UPLC-HRMS Derived Mass data for Ldt/Penem adducts.
Relative abundance denoted under masses in brackets.

| Protein | Drug | Protein MW (da) | Mass 1 (da) | Mass 2 (da) | Mass 3 (da) | Mass Difference (da) |
|---|---|---|---|---|---|---|
| Ldt$_{Mt2}$ | | 38085.5 | 38083 [45] | 38115 [75] | 38119 [100] | |
| Ldt$_{Mt2}$ | T400 | 38085.5 | 38118 [100] | 38097 [25] | 38170 [35] | +87 |
| Ldt$_{Mt2}$ | T402 | 38085.5 | 38118 [100] | 38137 [35] | 38169 [25] | +54<br>+86 |
| Ldt$_{Mab2}$ | | 37319.6 | 39486.5 [100] | 39668 [10] | | |

TABLE 2-continued

UPLC-HRMS Derived Mass data for Ldt/Penem adducts.
Relative abundance denoted under masses in brackets.

| Protein | Drug | Protein MW (da) | Mass 1 (da) | Mass 2 (da) | Mass 3 (da) | Mass Difference (da) |
|---|---|---|---|---|---|---|
| Ldt$_{Mab2}$ | T400 | 38085.5 | 39572.5 [100] | 39658 [20] | 39753 [5] | +86<br>+171.5<br>+266.5 |
| Ldt$_{Mab2}$ | T402 | 38085.5 | 39572.5 [100] | 39688 [20] | 39842 [10] | +86<br>+210.5<br>+355.5 |
| Ldt$_{Cl}$ | | 33767.4 | 33767.5 [100] | | | |
| Ldt$_{Cl}$ | T400 | 33767.4 | 33767.5 [100] | 33853.5 [70] | 34042.5 [20] | +86<br>+275 |
| Ldt$_{Cl}$ | T402 | 33767.4 | 33853.5 [15] | 34111.5 [40] | 34155 [100] | +344<br>+387.5 |
| Ldt$_{Kp}$ | | 33502.2 | 33532.5 [100] | | | |
| Ldt$_{Kp}$ | T400 | 33502.2 | 33532.5 [100] | 33618.5 [70] | 33868.5 [5] | +86<br>+336 |
| Ldt$_{Kp}$ | T402 | 33502.2 | 33532.5 [100] | 33875 [45] | 33920 [90] | +342.5<br>+387.5 |

Methods for Total Synthesis of Penems:
Scheme 1: Synthetic route to penems
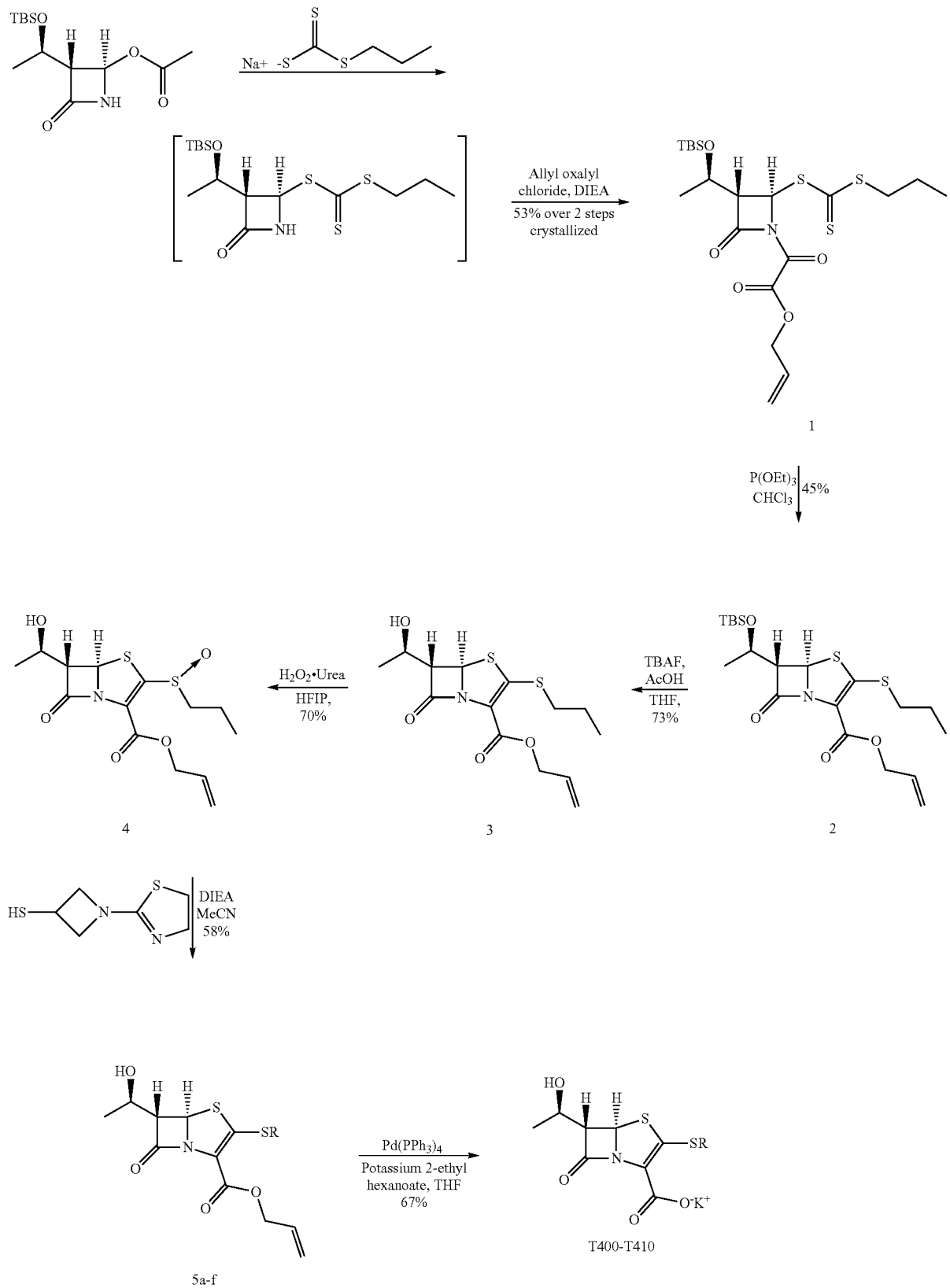

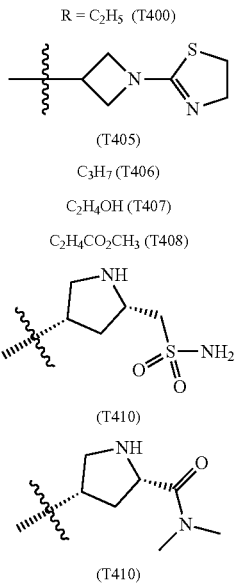

R = C₂H₅ (T400)

(T405)

C₃H₇ (T406)

C₂H₄OH (T407)

C₂H₄CO₂CH₃ (T408)

(T410)

(T410)

Allyl 2-((3R,4S)-3-((R)-1-((tert-butyldimethylsilyl)oxy)ethyl)-2-oxo-4-(((propylthio)carbonothioyl)thio)azetidin-1-yl)-2-oxoacetate (1)

The preparation of 1 followed the procedures of Brenek et al. (Brenek, et al., 2012). 1-propanethiol (20.7 mL, 223 mmol) in methyl tert-butyl ether (100 mL) was slowly added to a suspension of sodium hydride (14 g, 350 mmol) in methyl tert-butyl ether (500 mL) and the mixture was stirred for 1 h at which time carbon disulfide (20.93 mL, 348 mmol) was added and the resulting yellow slurry was stirred for 1 h. Magnesium sulfate (3 g) was added and the slurry was vacuum filtered under nitrogen through Celite to remove excess sodium hydride and the filter cake was rinsed with methyl tert-butyl ether. (WARNING! The Celite filter pad contains trace amounts of methyl tert-butyl ether in addition to large quantities of residual sodium hydride. This cake will spontaneously combust and on this scale can cause a significant flame. Great care must be taken to remove as much ether as possible. After filtering, keep the solids under nitrogen, suspend the filter cake in dichloromethane, cool to 0° C. and quench with isopropanol in the absence of oxygen). Transfer the filtrate to a clean flask and add (3R,4R)-4-acetoxy-3-[(R)-1-(tert-butyldimethylsilyloxy)ethyl]azetidin-2-one (50 g, 174 mmol) batchwise while stirring the solution rapidly. After 1 h, filter the slurry through a pad of silica gel. Wash the solids with methyl tert-butyl ether (200 mL). The filtrate is cooled to −10° C. in a brine/ice bath and allyl oxalyl chloride (50 mL, 400 mmol) was added followed by a solution of triethylamine (56 mL, 400 mmol) in methyl tert-butyl ether (100 mL). The reaction mixture was warmed to room temperature and stirred for 1 h before it was quenched with water (100 mL). The organic layer was separated and washed twice with sodium bicarbonate (100 mL), dried with anhydrous sodium sulfate, filtered, diluted with heptanes (250 mL) and concentrated in vacuo. Once the majority of solvent is removed, additional heptanes (250 mL) is added and concentrated in vacuo to completion to ensure that no methyl tert-butyl ether remains. The crude oil is dissolved in 400 mL isooctanes and crystallized at 4° C. for 16-24 h to provide 1 as yellow needles (45.8 g, 53%).

1: TLC (hexanes:ethyl acetate, 7:3)=0.4. MP=65-67° C. ¹H NMR (400 MHz, CDCl₃) δ=6.76 (dd, J=0.4, 3.5 Hz, 1H), 5.94 (tdd, J=6.1, 10.6, 17.0 Hz, 1H), 5.39 (qd, J=1.4, 17.0 Hz, 1H), 5.31 (qd, J=1.0, 10.4 Hz, 1H), 4.78 (qd, J=1.2, 6.1 Hz, 2H), 4.39 (dq, J=2.5, 6.3 Hz, 1H), 3.56 (dd, J=2.5, 3.5 Hz, 1H), 3.39 (dt, J=3.7, 7.2 Hz, 2H), 1.76 (sxt, J=7.4 Hz, 3H), 1.24 (d, J=6.5 Hz, 3H), 1.03 (t, J=7.4 Hz, 3H), 0.86 (s, 9H), 0.09 (s, 3H), 0.06 (s, 3H). ¹³C NMR (101 MHz, CDCl₃) □=218.3, 163.5, 159.1, 154.4, 130.4, 120.2, 67.4, 66.0, 64.5, 58.9, 38.9, 26.9, 25.6, 21.9, 21.3, 17.8, 13.4, −4.3, −5.3. HRMS (FAB), C₁₂H₃₄NO₅S₃Si [M+H⁺] calculated: 492.1368; found: 492.1370; Δ −0.3 ppm.

Allyl (5S,6R)-6-((R)-1-((tert-butyldimethylsilyl)oxy)ethyl)-7-oxo-3-(propylthio)-4-thia-1-azabicyclo[3.2.0]hept-2-ene-2-carboxylate (2)

The preparation of 2 followed the procedures of Brenek et al. (4). A solution of triethylphosphite (38.7 mL, 233 mmol) in anhydrous ethanol-free chloroform (450 mL) was added over 24 h to a refluxing, stirring solution of 1 (45.8 g, 93 mmol) in chloroform (1 L) using a 2 L round bottomed flask fitted with a Claisen adapter, reflux condenser and addition funnel. Once addition was complete, the solution was stirred for an additional 24 h, at which time additional triethyl phosphite (15 mL) was added in one portion. The mixture was stirred at reflux for 16 h, cooled to room temperature, and washed with aqueous HCl (0.1N, 250 mL), saturated aqueous sodium bicarbonate (250 mL) and brine. The organic fractions were concentrated in vacuo and purified by silica gel chromatography (hexanes) to ensure the removal of triethylphosphite. The product oil crystallized from isooctane to produce 2 as white needles (18.57 g, 45%).

2: TLC (hexanes:ethyl acetate, 7:3)=0.5. m.p.=104-105° C. ¹H NMR (400 MHz, CDCl₃) δ=5.93 (tdd, J=5.4, 10.7, 17.2 Hz, 1H), 5.59 (d, J=1.4 Hz, 1H), 5.40 (qd, J=1.6, 17.2 Hz, 1H), 5.22 (qd, J=1.4, 10.4 Hz, 1H), 4.70 (tddd, J=1.6, 5.5, 13.5, 28.2 Hz, 2H), 4.23 (td, J=6.1, 11.5 Hz, 1H), 3.66 (dd, J=1.6, 4.9 Hz, 1H), 2.91 (tdd, J=7.4, 12.5, 32.3 Hz, 2H), 1.74 (sxt, J=7.4 Hz, 2H), 1.25 (d, J=6.3 Hz, 3H), 1.03 (t, J=7.3 Hz, 3H), 0.88 (s, 9H), 0.07 (s, 3H), 0.07 (s, 3H). ¹³C NMR (101 MHz, CDCl$_3$) δ=172.1, 159.8, 131.9, 118.1, 117.0, 71.4, 65.3, 63.7, 37.9, 25.7, 23.3, 22.5, 17.9, 13.2, −4.3, −5.1. HRMS (FAB), C$_{20}$H$_{33}$NO$_4$S$_2$Si [M$^+$] calculated: 443.1620; found: 443.1624; Δ −0.7 ppm.

Allyl (5S,6R)-6-((R)-1-hydroxyethyl)-7-oxo-3-(propylthio)-4-thia-1-azabicyclo[3.2.0]hept-2-ene-2-carboxylate (3)

A solution of 2 (10.2 g, 22.99 mmol) in tetrahydrofuran (64 mL) was added to a mixture of tetra-N-butylammonium fluoride (34.5 mmol) and acetic acid (12.5 mL, 218 mmol) in tetrahydrofuran (64 mL). The reaction mixture was stirred for 24 h before it was washed with saturated aqueous sodium bicarbonate. The aqueous layer was back extracted with dichloromethane and the combined organic layers were washed with brine, dried with anhydrous sodium sulfate, filtered and concentrated in vacuo. The crude product was purified by silica gel chromatography (hexanes:ethyl acetate, 1:1) and the resulting oil crystallized from ethyl acetate/isooctane to provide 3 (5.5 g, 73%).

3: TLC (hexanes:ethyl acetate, 7:3)=0.2. m.p.=85-86° C. $^1$H NMR (400 MHz, CDCl$_3$) δ=5.95 (tdd, J=5.4, 10.6, 17.2 Hz, 1H), 5.63 (d, J=1.6 Hz, 1H), 5.41 (qd, J=1.5, 17.2 Hz, 1H), 5.23 (qd, J=1.4, 10.6 Hz, 1H), 4.78 (tdd, J=1.5, 5.4, 13.5 Hz, 1H), 4.66 (tdd, J=1.4, 5.6, 13.5 Hz, 1H), 4.24 (quin, J=6.5 Hz, 1H), 3.70 (dd, J=1.4, 6.8 Hz, 1H), 2.98 (td, J=7.4, 12.7 Hz, 1H), 2.88 (td, J=7.2, 12.5 Hz, 1H), 1.74 (sxt, J=7.4 Hz, 2H), 1.35 (d, J=6.3 Hz, 3H), 1.03 (t, J=7.3 Hz, 3H). $^{13}$C NMR (101 MHz, CDCl$_3$) δ=172.1, 159.8, 156.2, 131.9, 118.2, 116.7, 70.9, 65.5, 65.5, 64.0, 37.9, 23.3, 21.9, 13.2. HRMS (FAB), C$_{14}$H$_{19}$NO$_4$S$_2$[M$^+$] calculated: 329.0756; found: 329.0753; Δ 0.8 ppm.

Allyl (5S,6R)-6-((R)-1-hydroxyethyl)-7-oxo-3-(propylsulfinyl)-4-thia-1-azabicyclo[3.2.0]hept-2-ene-2-carboxylate (4)

Urea•hydrogen peroxide (1.62 g, 16.7 mmol) was dissolved in 1,1,1,3,3,3-hexafluoroisopropanol (16 mL) and added to a solution of 3 (5.0 g, 15.2 mmol) 1,1,1,3,3,3-hexafluoroisopropanol (20 mL) in one portion and the solution was stirred for 24 h. Heptanes (50 mL) was added to the product mixture and concentrated in vacuo. The process was repeated as necessary to remove all traces of fluorinated solvent prior to purification by silica gel chromatography (hexanes:ethyl acetate, 1:1). The resulting oil recrystallized from ethyl acetate/isooctane to provide 4 as a mixture of diasteromeric sulfoxides as yellow needles (4.63 g, 88%).

4: TLC (hexanes:ethyl acetate, 1:1)=0.2. m.p.=90-93° C. $^1$H NMR (400 MHz, CDCl$_3$) δ=5.98-5.87 (m, 1H), 5.86 (d, J=1.8 Hz, 0.33H), 5.71 (d, J=1.8 Hz, 0.67H), 5.41 (qd, J=1.6, 17.0 Hz, 0.33H), 5.43 (qd, J=1.4, 17.2 Hz, 0.66H), 5.29 (qd, J=1.2, 10.6 Hz, 1H), 4.77 (qdd, J=1.6, 5.5, 13.3 Hz, 1H), 4.67 (qdd, J=1.6, 5.7, 13.3 Hz, 1H), 4.27-4.14 (m, 1H), 3.92 (dd, J=1.6, 6.8 Hz, 0.66H), 3.88 (dd, J=2.0, 7.0 Hz, 0.33H), 3.21-3.04 (m, 1H), 2.99 (ddt, J=7.0, 9.2, 13.3 Hz, 1H), 2.04-1.77 (m, 2H), 1.35 (d, J=6.3 Hz, 3H), 1.11 (t, J=7.4 Hz, 3H). $^{13}$C NMR (101 MHz, CDCl$_3$) δ=172.7, 171.5, 164.4, 164.0, 158.2, 158.1, 130.8, 121.6, 121.4, 119.5, 119.5, 73.2, 73.2, 66.7, 66.7, 65.6, 65.4, 65.4, 63.4, 57.5, 57.0, 21.8, 16.5, 16.1, 13.0.

General Procedure for the Addition of C-2 Thiol Side Chains to the 2-Ethylsulfinyl Penem:

Allyl (5S,6R)-3-((1-(4,5-dihydrothiazol-2-yl)azetidin-3-yl)thio)-6-((R)-1-hydroxyethyl)-7-oxo-4-thia-1-azabicyclo[3.2.0]hept-2-ene-2-carboxylate (5b)

A solution of 1-(4,5-dihydro-2-thiazolyl)-3-azetidinethiol hydrochloride (3.10 g, 14.74 mmol) in acetonitrile (50 mL) followed by diisopropylethylamine (3.70 mL, 20.77 mmol) were added to a stirring solution of 4 (4.63 g, 13.4 mmol) in acetonitrile (100 mL) and the mixture was stirred for 2 h at 0° C. The solution was diluted with brine and the aqueous layer was back extracted three times with ethyl acetate. The combined organic layers were dried with anhydrous sodium sulfate, filtered and concentrated in vacuo. The crude oil was purified by silica gel chromatography (methanol:dichloromethane, 1:40) to provide 5b as a yellow oil that became a glass under high vacuum (2.85 g, 50%).

5b: TLC (methanol:dichloromethane, 1:19)=0.3. $^1$H NMR (400 MHz, CDCl$_3$) □=5.94 (tdd, J=5.4, 10.7, 17.2 Hz, 1H), 5.69 (d, J=1.4 Hz, 1H), 5.41 (qd, J=1.5, 17.1 Hz, 1H), 5.24 (qd, J=1.2, 10.5 Hz, 1H), 4.77 (tdd, J=1.4, 5.5, 13.4 Hz, 1H), 4.67 (tdd, J=1.4, 5.6, 13.4 Hz, 1H), 4.40 (td, J=8.4, 23.9 Hz, 3H), 4.19 (sxt, J=6.5 Hz, 1H), 4.25-4.10 (m, 1H), 4.00 (t, J=7.4 Hz, 2H), 4.06-3.90 (m, 2H), 3.72 (dd, J=1.5, 6.9 Hz, 1H), 3.36 (t, J=7.4 Hz, 2H), 1.33 (d, J=6.5 Hz, 3H). $^{13}$C NMR (101 MHz, CDCl$_3$) δ=172.2, 164.4, 159.5, 152.1, 131.6, 118.5, 117.6, 71.5, 65.8, 65.2, 65.0, 60.4, 59.3, 58.7, 36.2, 36.1, 21.9. HRMS (FAB), C$_{17}$H$_{22}$N$_3$O$_4$S$_3$ [M+H$^+$] calculated: 428.0773; found: 428.0765; Δ 1.8 ppm.

Allyl (5R,6S)-6-((R)-1-hydroxyethyl-3-(ethylthio)-7-oxo-4-thia-1-azabicyclo[3.2.0]hept-2-ene-2-carboxylate (5a)

TLC (methanol:ethyl acetate, 3:17)=0.9. $^1$H NMR (400 MHz, CDCl$_3$) δ=5.96 (tdd, J=5.4, 10.7, 17.2 Hz, 1H), 5.64 (d, J=1.6 Hz, 1H), 5.42 (qd, J=1.6, 17.2 Hz, 1H), 5.24 (qd, J=1.6, 10.4 Hz, 1H), 4.79 (tdd, J=1.4, 5.4, 13.4 Hz, 1H), 4.67 (tdd, J=1.5, 5.5, 13.5 Hz, 1H), 4.25 (quin, J=6.5 Hz, 1H), 3.71 (dd, J=1.4, 6.8 Hz, 1H), 3.01 (qd, J=7.2, 12.3 Hz, 1H), 2.94 (qd, J=7.2, 12.5 Hz, 1H), 1.37 (t, J=7.2 Hz, 3H), 1.36 (d, J=6.3 Hz, 3H).

Allyl (5R,6S)-6-((R)-1-hydroxyethyl)-3-((2-hydroxyethyl)thio)-7-oxo-4-thia-1-azabicyclo[3.2.0]hept-2-ene-2-carboxylate (5c)

$^1$H NMR (400 MHz, CHCl$_3$) δ=5.95 (ddt, J=5.4, 10.5, 17.2, 1H), 5.65 (d, J=1.4 Hz, 1H), 5.41 (qd, J=1.5, 17.2 Hz, 1H), 5.24 (qd, J=1.3, 9.0 Hz, 1H), 4.78 (tdd, J=1.4, 5.4, 13.4 Hz, 1H), 4.66 (tdd, J=1.3, 5.6, 13.4 Hz, 1H), 4.23 (quin, J=6.5 Hz, 1H), 3.86 (t, J=6.2 Hz, 2H), 3.71 (dd, J=1.5, 6.8 Hz, 1H), 3.14 (tq, J=6.3, 14.0 Hz, 1H), 1.35 (d, J=6.3 Hz, 3H). $^{13}$C NMR (101 MHz, CHCl$_3$) δ=172.2, 159.8, 156.3, 131.8, 118.2, 116.7, 70.95, 65.4, 64.0, 37.8, 23.2, 21.7, 13.1.

Allyl (5R,6S)-6-((R)-1-hydroxyethyl)-3-((3-methoxy-3-oxopropyl)thio)-7-oxo-4-thia-1-azabicyclo[3.2.0]hept-2-ene-2-carboxylate (5d)

$^1$H NMR (400 MHz, CHCl$_3$) δ=5.97 (ddt, J=5.3, 11.7, 17.2, 1H), 5.66 (d, J=1.4 Hz, 1H), 5.40 (qd, J=1.5, 17.2 Hz, 1H), 5.23 (qd, J=1.3, 10.5 Hz, 1H), 4.77 (tdd, J=1.4, 5.4, 13.4 Hz, 1H), 4.65 (tdd, J=1.4, 5.5, 13.4 Hz, 1H), 4.23 (quin, J=6.4 Hz, 1H), 3.72 (m, 1H), 3.71 (s, 3H), 3.21 (tq, J=4.7, 11.7, 2H), 2.75 (m, 2H), 1.34 (d, J=6.4 Hz, 3H). $^{13}$C NMR (101 MHz, CHCl$_3$) δ=171.9, 171.2, 159.6, 154.1, 131.8, 118.3, 117.6, 71.2, 65.6, 64.3, 52.1, 34.6, 30.6, 21.9, 21.1.

Allyl (5R,6S)-6-((R)-1-hydroxyethyl)-3-(((3R,5R)-1-(((4-nitrobenzyl)oxy)carbonyl)-5-((sulfamoylamino)methyl)pyrrolidin-3-yl)thio)-7-oxo-4-thia-1-azabicyclo[3.2.0]hept-2-ene-2-carboxylate (5e)

TLC (hexanes:ethyl acetate, 1:1)=0.15. $^1$H NMR (400 MHz, MeOD) δ=8.21 (d, J=8.6 Hz, 2H), 7.56 (d, J=6.1 Hz, 2H), 6.00-5.79 (m, 1H), 5.67 (d, J=2.3 Hz, 1H), 5.37 (qd, J=1.6, 17.0 Hz, 2H), 5.21 (qd, J=1.0, 7.8 Hz, 1H), 5.27-5.15 (m, 2H), 4.28-4.15 (m, 1H), 3.85-3.72 (m, 1H), 3.70 (dd, J=0.8, 7.0 Hz, 1H), 3.48-3.32 (m, 2H), 2.69-2.54 (m, 2H), 1.28 (d, J=6.3 Hz, 3H). $^{13}$C NMR (101 MHz, 1:1 CHCl$_3$:MeOD) δ=172.48, 159.3, 156.6, 146.8, 131.2, 127.6, 127.4, 122.9, 117.0, 115.6, 70.4, 65.0, 64.6, 64.4, 63.8, 57.2, 37.0, 33.5, 22.6, 20.4, 12.1.

Allyl (5R,6S)-3-(((3R,5R)-5-(dimethylcarbamoyl)-1-(((4-nitrobenzyl)oxy)carbonyl)pyrrolidin-3-yl)thio)-6-((R)-1-hydroxyethyl)-7-oxo-4-thia-1-azabicyclo[3.2.0]hept-2-ene-2-carboxylate (5f)

TLC (hexanes:ethyl acetate, 1:1)=0.15. $^1$H NMR (400 MHz, CDCl$_3$) δ=8.17 (d, J=9.6 Hz, 2H), 7.50 (d, J=8.8 Hz, 2H), 5.91 (tdd, J=5.7, 10.4, 17.0 Hz, 1H), 5.66 (d, J=1.4 Hz, 1H), 5.46-5.32 (m, 1H), 5.31-5.24 (m, 1H), 5.12-4.96 (m, 1H), 4.83-4.72 (m, 2H), 4.65 (td, J=13.5, 17.2 Hz, 2H), 4.36-4.22 (m, 1H), 4.22-4.13 (m, 1H), 4.13-3.98 (m, 1H), 3.69 (dd, J=1.5, 7.1 Hz, 1H), 3.60-3.31 (m, 3H), 3.08 (s, 3H), 2.96 (s, 3H), 2.83-2.68 (m, 1H), 2.64 (d, J=11.9 Hz, 1H), 2.05-1.79 (m, 2H), 1.31 (d, J=6.5 Hz, 3H). $^{13}$C NMR (101 MHz, 1:1 CHCl$_3$:MeOD) δ=172.5, 171.4, 171.2, 156.5, 153.4, 152.9, 146.9, 143.4, 131.3, 127.4, 123.0, 117.2, 65.2, 56.4, 56.2, 55.6, 55.3, 40.2, 39.4, 36.2, 35.3, 34.4, 33.8, 12.3.

General Procedure for Allyl Deprotection with Palladium (II) Acetate:

(5R,6S)-3-(ethylsulfinyl)-6-((R)-1-hydroxyethyl)-7-oxo-4-thia-1-azabicyclo[3.2.0]hept-2-ene-2-carboxylate (T400)

Palladium(II) acetate (1 mg, 0.003 mmol) and triethylphosphite (3.8 μL, 0.022 mmol) were sequentially added to a mixture of sodium bicarbonate (5.9 mg, 0.07 mmol), 5,5-dimethyl-cyclohexane-1,3-dione (5.9 mg, 0.042 mmol), water (168 μL) and tetrahydrofuran (422 μL) and vigorously stirred for 5 min. A solution of 5a (20 mg, 0.063 mmol) in tetrahydrofuran (85 μL) was added, and the reaction mixture was stirred while heating to 35° C. for 45 min. The solution was diluted with water (500 μL) and dichloromethane (400 μL), washed three times with dichloromethane (5 mL) and the aqueous layer was added directly to a column of Diaion polystyrene resin (5 mL) and was eluted with water and the product-containing fractions were lyophilized to provide T400 as a white powder.

T400: $^1$H NMR (400 MHz, D$_2$O) δ=5.72 (d, J=1.4 Hz, 1H), 4.25 (quin, J=6.3 Hz, 1H), 3.95 (dd, J=1.4, 5.9 Hz, 1H), 3.14-2.90 (m, 2H), 1.34 (t, J=7.3 Hz, 3H), 1.31 (d, J=6.5 Hz, 3H). HRMS (FAB), C$_{10}$H$_{12}$NO$_4$S$_2$ [M–H$^+$] calculated: 274.0208; found: 274.0211; Δ 1.1 ppm.

A General Procedure for Deallylation with Palladium Tetrakis:

Potassium (5S,6R)-3-((1-(4,5-dihydrothiazol-2-yl)azetidin-3-yl)thio)-6-((R)-1-hydroxyethyl)-7-oxo-4-thia-1-azabicyclo[3.2.0]hept-2-ene-2-carboxylate (T405)

Palladium tetrakis (43 mg, 0.21 mmol) was added to a solution of 5b (1.8 g, 4.21 mmol) in freshly distilled tetrahydrofuran (84 mL) at which time the mixture became cloudy. A solution of potassium 2-ethylhexanoate (873 mg, 4.0 mmol) in tetrahydrofuran (16.8 mL) was added causing the reaction mixture to initially become clear. After stirring for 30 min, the solution became cloudy with the formation of yellow crystalline leaves. The reaction mixture is cooled to 4° C. and stirred for an additional 2 h. The precipitate is filtered and washed with cold tetrahydrofuran to provide T405 as an off-white powder (1.2 g, 66%). The precipitate may be re-dissolved in water and washed with dichloromethane to remove trace quantities of 5b and triphenylphosphine; the major impurities of the reaction. No evidence of palladium contamination was found by HRMS.

T405: $^1$H NMR (400 MHz, D$_2$O) δ=5.71 (d, J=1.0 Hz, 1H), 4.50 (td, J=8.4, 20.9 Hz, 2H), 4.24 (quin, J=6.5 Hz, 1H), 4.32-4.18 (m, 1H), 4.02 (ddd, J=4.8, 9.0, 19.1 Hz, 2H), 3.93 (t, J=8.0 Hz, 2H), 3.96-3.84 (m, 1H), 3.45 (t, J=7.4 Hz, 2H), 1.30 (d, J=6.5 Hz, 3H). $^{13}$C NMR (101 MHz, D$_2$O) δ=175.4, 166.4, 143.6, 124.1, 69.4, 64.7, 63.8, 59.4, 59.0, 57.7, 51.1, 35.6, 35.1, 20.1. HRMS (UPLC), C$_{14}$H$_{18}$N$_3$O$_4$S$_3$ [M+H$^+$] calculated: 388.0456; found: 388.0457; Δ 0.3 ppm.

Potassium (5R,6S)-6-((R)-1-hydroxyethyl)-3-propylthio-7-oxo-4-thia-1-azabicyclo[3.2.0]hept-2-ene-2-carboxylate (T406)

From 3; $^1$H NMR (400 MHz, D$_2$O) δ=5.66 (d, J=1.2 Hz, 1H), 4.25 (quin, J=6.3 Hz, 1H), 3.89 (dd, J=1.3, 6.0 Hz, 1H), 3.05-2.92 (m, 1H), 2.85 (td, J=7.4, 13.0 Hz, 1H), 1.71 (dqd, J=2.6, 7.3, 14.5 Hz, 2H), 1.31 (d, J=6.5 Hz, 3H), 0.99 (t, J=7.4 Hz, 3H). $^{13}$C NMR (101 MHz, D$_2$O) δ=175.6, 166.8, 147.1, 123.3, 69.1, 64.7, 62.9, 37.2, 23.2, 20.1, 12.3. HRMS (UPLC), C$_{11}$H$_{15}$NO$_4$S$_2$Na [M+Na$^+$] calculated: 312.0340; found: 312.0341; Δ 0.3 ppm.

Potassium (5R,6S)-6-((R)-1-hydroxyethyl)-3-((2-hydroxyethyl)thio)-7-oxo-4-thia-1-azabicyclo[3.2.0]hept-2-ene-2-carboxylate (T407)

From 5c; $^1$H NMR (400 MHz, D$_2$O) δ=5.67 (d, J=1.4 Hz, 1H), 4.25 (quin, J=6.3 Hz, 1H), 3.91 (dd, J=1.5, 6.0 Hz, 1H), 3.82 (dt, J=0.6, 6.5 Hz, 2H), 3.16 (td, J=6.0, 14.1 Hz, 1H), 3.03 (td, J=6.6, 14.1 Hz, 1H), 1.30 (d, J=6.5 Hz, 3H). HRMS (UPLC), C$_{10}$H$_{14}$NO$_5$S$_2$ [M+H$^+$] calculated: 292.0308; found: 292.0297; Δ 3.1 ppm.

Potassium (5R,6S)-6-((R)-1-hydroxyethyl)-3-((3-methoxy-3-oxopropyl)thio)-7-oxo-4-thia-1-azabicyclo[3.2.0]hept-2-ene-2-carboxylate (T408)

From 5d; $^1$H NMR (400 MHz, D$_2$O) δ=5.69 (d, J=1.8 Hz, 1H), 4.25 (quin, J=6.3 Hz, 1H), 3.92 (dd, J=1.5, 6.0 Hz, 1H), 3.72 (s, 3H), 3.25 (td, J=6.9, 14.0 Hz, 1H), 3.10 (td, J=7.1, 14.1 Hz, 1H), 2.83 (dt, J=1.8, 6.7 Hz, 2H), 1.31 (d, J=6.5 Hz, 3H). HRMS (UPLC), C$_{12}$H$_{16}$NO$_6$S$_2$ [M+H$^+$] calculated: 334.0414; found: 334.0410; Δ 1.2 ppm.

Potassium (5R,6S)-6-((R)-1-hydroxyethyl)-7-oxo-3-(((3R,5R)-5-((sulfamoylamino)methyl)pyrrolidin-3-yl)thio)-4-thia-1-azabicyclo[3.2.0]hept-2-ene-2-carboxylate (T409)

From 5e; $^1$H NMR (400 MHz, D$_2$O) δ=5.71 (d, J=1.4 Hz, 1H), 4.25 (quin, J=6.4 Hz, 1H), 4.15-4.03 (m, 1H), 3.95 (dd, J=1.5, 6.0 Hz, 1H), 3.81-3.70 (m, 2H), 3.64 (dd, J=3.7, 11.7 Hz, 1H), 3.70-3.60 (m, 1H), 3.51 (dd, J=7.0, 11.5 Hz, 1H), 3.49 (dd, J=5.5, 7.4 Hz, 1H), 3.38 (dd, J=8.6, 15.5 Hz, 1H), 2.76-2.64 (m, 1H), 1.30 (d, J=6.5 Hz, 3H). HRMS (UPLC), C$_{13}$H$_{21}$N$_4$O$_6$S$_3$ [M+H$^+$] calculated: 425.0618; found: 425.0617; Δ 0.2 ppm.

Potassium (5R,6S)-3-(((3R,5R)-5-(dimethylcarbamoyl)pyrrolidin-3-yl)thio)-6-((R)-1-hydroxyethyl)-7-oxo-4-thia-1-azabicyclo[3.2.0]hept-2-ene-2-carboxylate (T410)

From 5f $^1$H NMR (400 MHz, D$_2$O) δ=5.69 (d, J=1.4 Hz, 1H), 4.25 (quin, J=6.3 Hz, 1H), 4.10 (q, J=7.0 Hz, 1H), 3.91 (dd, J=1.4, 6.3 Hz, 1H), 3.74 (dd, J=3.9, 5.3 Hz, 2H), 3.64 (dd, J=4.3, 5.1 Hz, 2H), 3.06 (s, 3H), 2.96 (s, 3H), 1.32 (d, J=6.8 Hz, 3H). HRMS (UPLC), C$_{15}$H$_{22}$N$_3$O$_5$S$_2$ [M+H$^+$] calculated: 388.0995; found: 388.0994; Δ 0.3 ppm.

Example 3

Results

Interactions Between L,D-Transpeptidases and β-Lactams.

Faropenem and the carbapenems doripenem, biapenem, and tebipenem exhibit in vitro bactericidal activity against *M. tuberculosis*, even without co-exposure of the bacteria to a β-lactamase inhibitor has previously demonstrated (Dhar, et al., 2015; Kaushik, et al., 2015). To identify the β-lactam that is most reactive with L,D-transpeptidases, the *M. tuberculosis* Ldt$_{Mt1}$ and Ldt$_{Mt2}$ enzymes were incubated with equimolar mixtures of faropenem, doripenem, biapenem and tebipenem and assessed the identities and abundance of acyl-enzyme adducts (created when the β-lactam ring reacts with the active site cysteine) using ultra performance liquid chromatography-mass spectrometry (UPLC-MS). Although each carbapenem produced a unique adduct when reacted individually with the L,D-transpeptidases, acylation by faropenem was the only adduct detected in the competition assays with the carbapenem mixture, indicating that the Ldt$_{Mt1}$ and Ldt$_{Mt2}$ enzymes preferentially bound faropenem over the other tested carbapenems (FIG. 6).

Figure 1A:
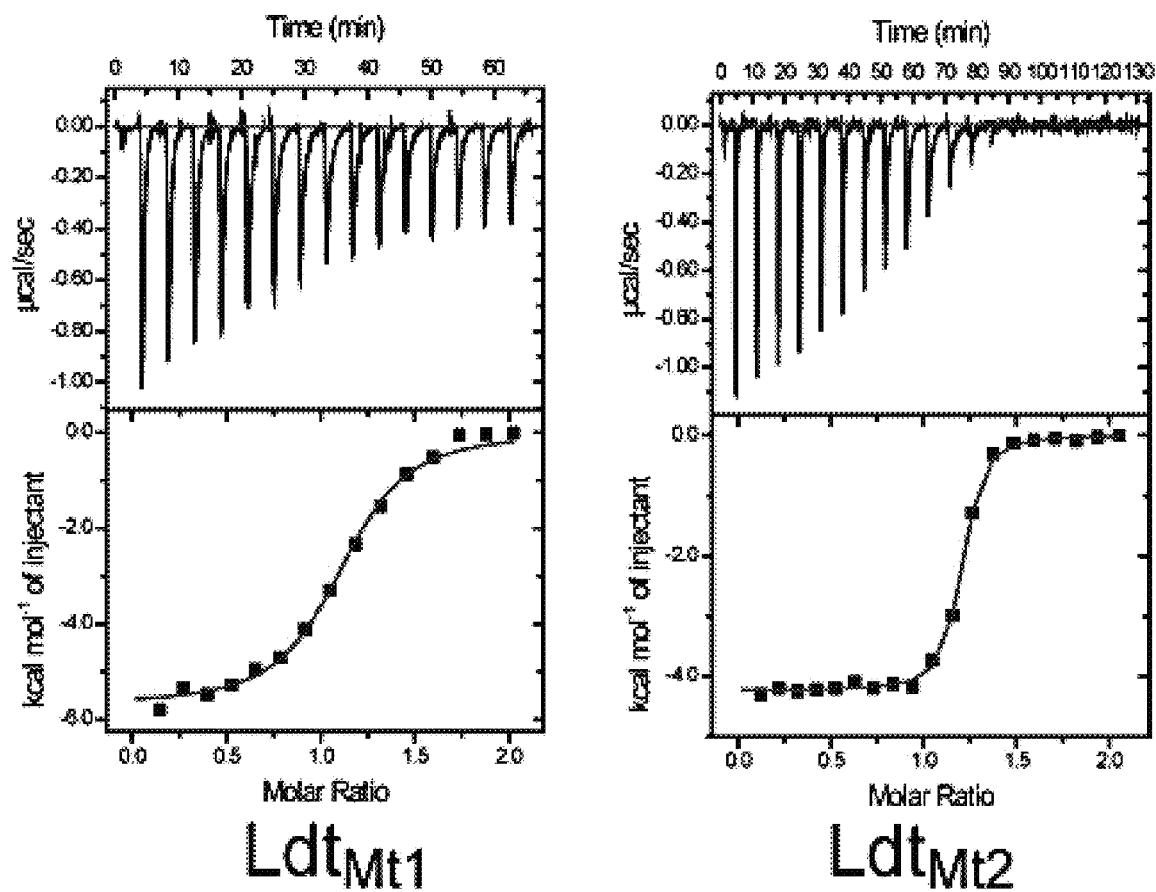
Figure 1A:
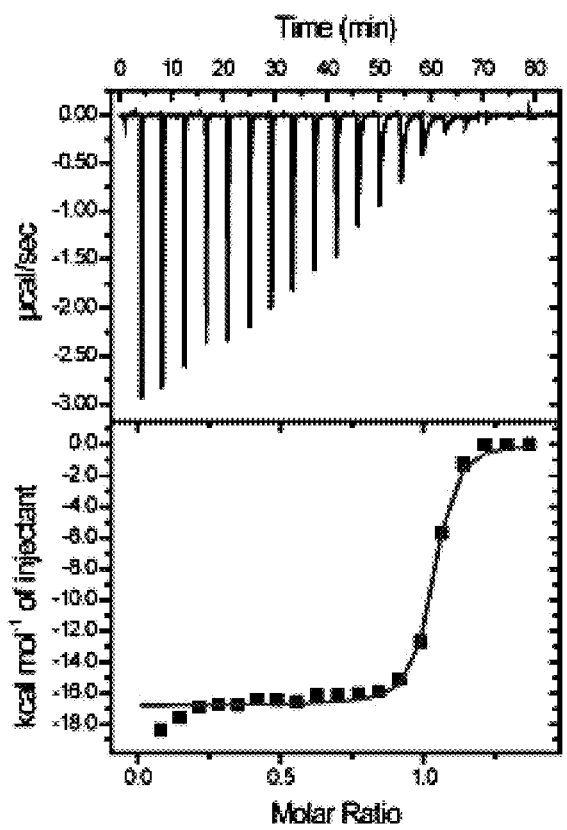
Figure 1A:
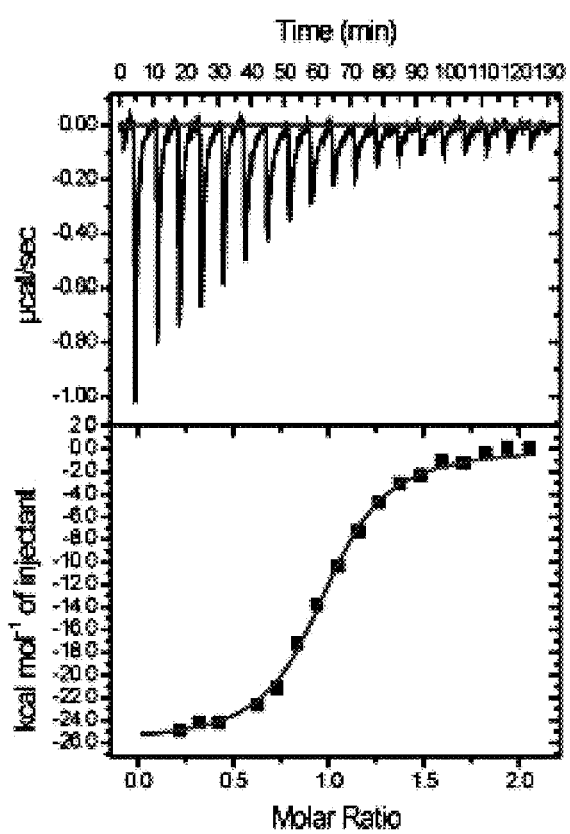

As a control, these enzymes were also reacted with equimolar mixtures of faropenem and the non-carbapenem β-lactams amoxicillin, cephalothin, and aztreonam. In the control mixture, the faropenem adduct (+86 Da) was the only acyl-adduct detected, confirming that the *M. tuberculosis* L,D-transpeptidases preferentially bound faropenem over non-carbapenem β-lactams (FIG. 6). Finally, the faropenem adduct was again the only species detected when an equimolar mixture of oxacillin, cephalexin and faropenem was reacted with Ldt$_{Mt2}$ or a penicillin binding protein DacB2 (results not shown). Additionally, while carbenicillin failed to bind to Ldt$_{Mt2}$ it formed a +379 Da adduct with DacB2. These L,D-transpeptidase/β-lactam interactions were also evaluated by isothermal titration calorimetry (ITC). While enzyme inactivation in these cases is irreversible, the absence of ITC response has been taken as evidence of no detectable binding and inactivation, whereas a positive response would reflect the sum of binding and subsequent chemical steps. Using this method, while tebipenem and faropenem exhibited single-modality binding to Ldt$_{Mt1}$ or Ldt$_{Mt2}$ with high affinity, the non-(carba)penem β-lactams either did not bind at all or interacted with reduced affinity to the enzymes (FIG. 1A).

As the *M. tuberculosis* L,D-transpeptidases clearly demonstrated preferential binding to (carba)penems, it was investigated whether this drug class also could target L,D-transpeptidases from other bacterial pathogens, thus potentially having wider use as an antibacterial agent. Using a comparative genomics approach, two L,D-transpeptidase orthologues in the acid-fast bacillus *Mycobacterium abscessus* (Ldt$_{Mab1}$, Ldt$_{Mab2}$) and one orthologue each in the following Gram-negative ESKAPE pathogens: *Klebsiella pneumoniae* (Ldt$_{Kp}$), *Enterobacter cloacae* (Ldt$_{Cl}$), and *Pseudomonas aeruginosa* (Ldt$_{Pa}$) were identified and subsequently cloned (results not shown). UPLC-MS assessment of acyl adduct formation induced by interaction of β-lactams with each of these enzymes revealed that these L,D-transpeptidases also preferentially reacted with faropenem over both the non-carbapenems and carbapenems tested (Table 1). Binding of the L,D-transpeptidases orthologs in *M. abscessus*, Ldt$_{Mab1}$ and Ldt$_{Mab2}$, to faropenem and tebipenem, and lack of binding to the non-carbapenems, was also confirmed by ITC (FIG. 1A). The data thus suggest that L,D-transpeptidases from diverse bacterial species, including ESKAPE pathogens, can be targeted with select (carba)penems.

Figure 1B:
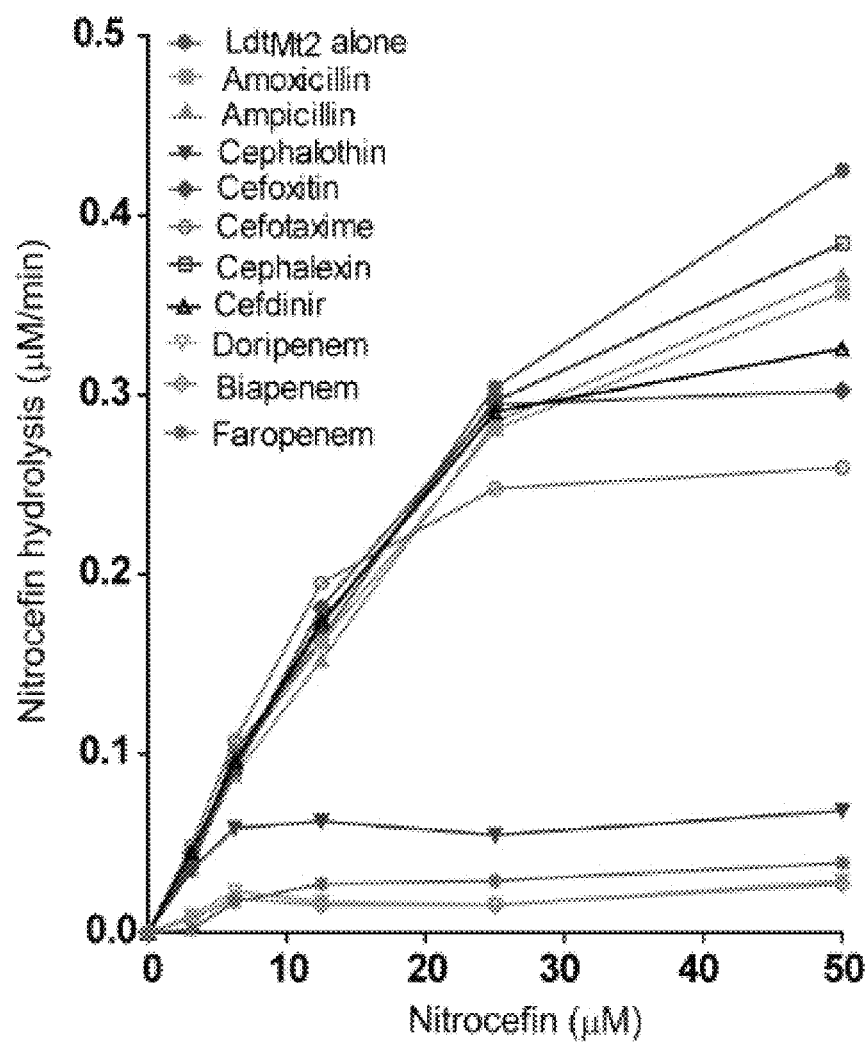

As an additional verification, the activity of Ldt$_{Mt2}$ following incubation with penicillins (amoxicillin and ampicillin), cephalosporins (cefoxitin, cefotaxime, cephalexin, cephalothin and cefdinir), and carbapenems (doripenem and biapenem) and the penem faropenem has been assessed. While doripenem, biapenem and faropenem robustly inhibited the ability of Ldt$_{Mt2}$ to hydrolyze nitrocefin, only one cephalosporin, namely cephalothin, showed comparable inhibitory activity and the remaining cephalosporins and penicillins exhibited little or no effect on the enzyme (FIG. 1B). Next, the hypothesis that if carbapenems derive their potency by inhibiting L,D-transpeptidases, then sensitivity of a *M. tuberculosis* mutant lacking Ldt$_{Mt2}$ would not be significantly affected compared to the wild-type strain has been tested. While the minimum inhibitory concentration (MIC$_{90}$) of carbenicillin, methicillin, oxacillin, cefdinir, cefotaxime and cephalexin was 16->32 fold higher for wild-type *M. tuberculosis*, MIC$_{90}$ of meropenem, doripenem, tebipenem and faropenem were only 2-8 fold different between the two strains (results not shown).

In Vivo Anti-TB Activity of Faropenem and Biapenem.

Figure 1C:
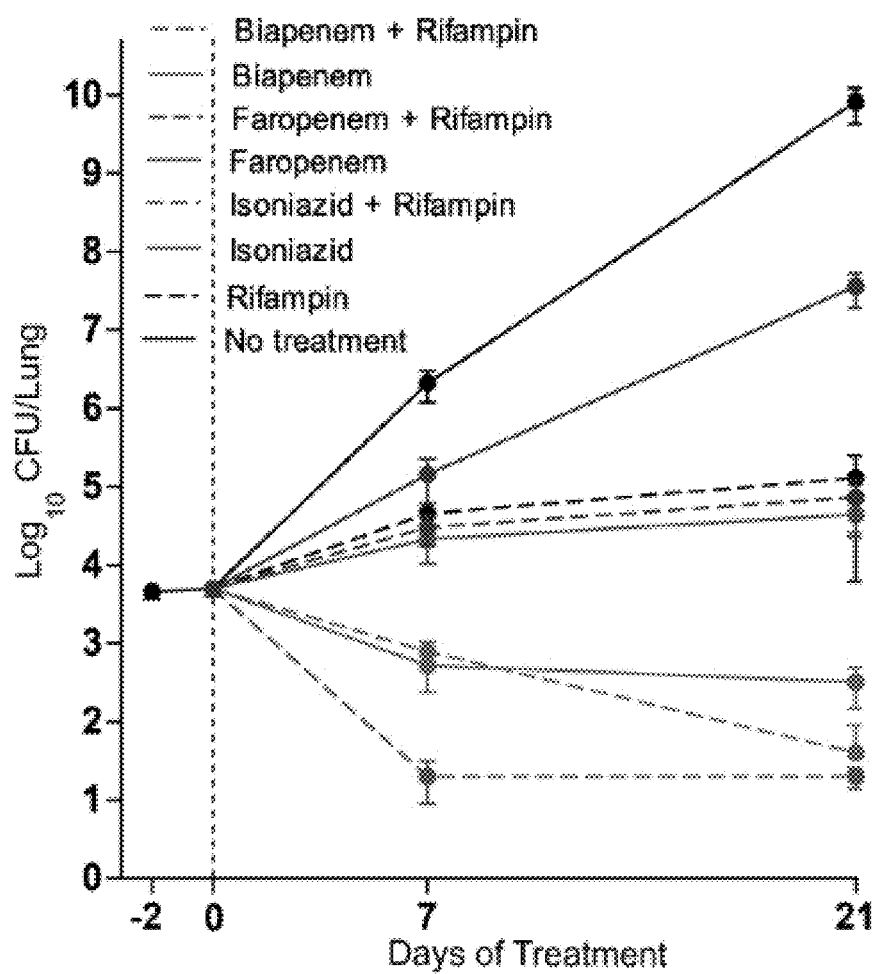

The anti-TB activity of faropenem observed in vitro, including potent bactericidal activity against *M. tuberculosis* (Kaushik, et al., 2015) and specific inhibitory interactions with the Ldt$_{Mt1}$ and Ldt$_{Mt2}$ enzymes, prompted us to evaluate the in vivo activity of this drug in a preclinical mouse model of TB treatment. The in vivo anti-TB activity of biapenem was also evaluated, which has a very good in vitro bactericidal activity against *M. tuberculosis* (Kaushik, et al., 2015). The antimicrobial activities of faropenem and biapenem were assessed in *M. tuberculosis*-infected BALB/c mice, and these drugs were administered both alone and in combination with rifampin, a key first-line anti-TB drug. Mice were infected by aerosol with *M. tuberculosis* H37Rv with an implantation of 3.7 log$_{10}$ colony-forming units (CFUs) in the lungs; treatment was initiated two days after infection and administered daily for three weeks. As expected, the untreated control mice developed severe disease and either died or were moribund by eighteen days post-infection. Also as expected, the bacterial load in the lungs of mice receiving isoniazid-containing control regimens decreased significantly during the first week of treatment (FIG. 1C). Administration of biapenem alone resulted in bacteriostatic activity as bacterial multiplication in the lungs was inhibited compared to the lungs of untreated control mice. Bacteriostatic activity was also observed in the lungs of mice treated with the faropenem-rifampin regimen. However, potent bactericidal activity was observed in the lungs of mice that received the biapenem-rifampin regimen, which resulted in a greater decline in lung CFUs than was obtained with the isoniazid-rifampin positive control regimen. Furthermore, administration of both faropenem and biapenem, either alone or in combination with rifampin, prevented the development of gross lung lesions in the infected mice (FIG. 1D-K.

Structures of L,D-Transpeptidases with (Carba)Penems.

Figure 2A:
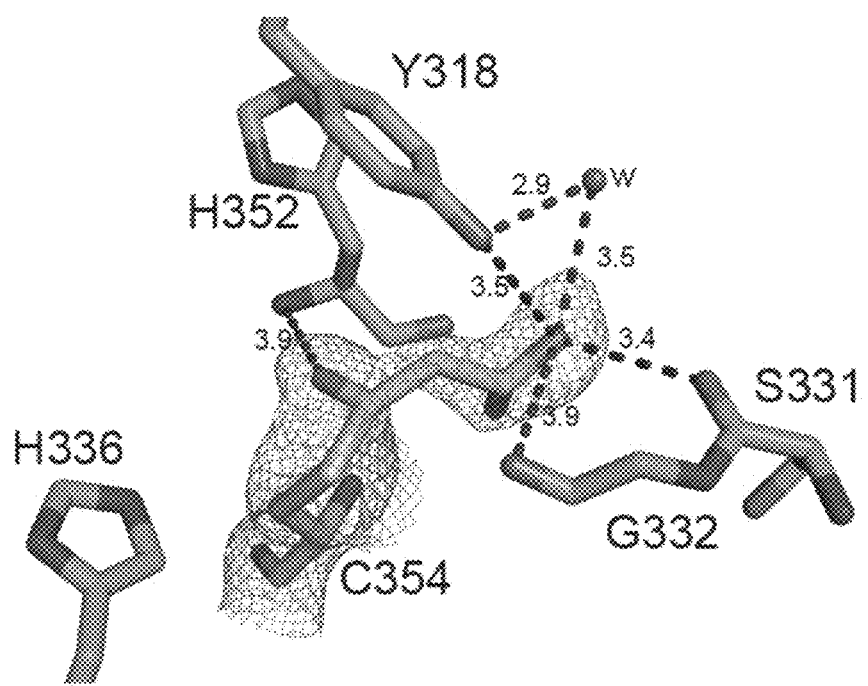
Figure 2B:
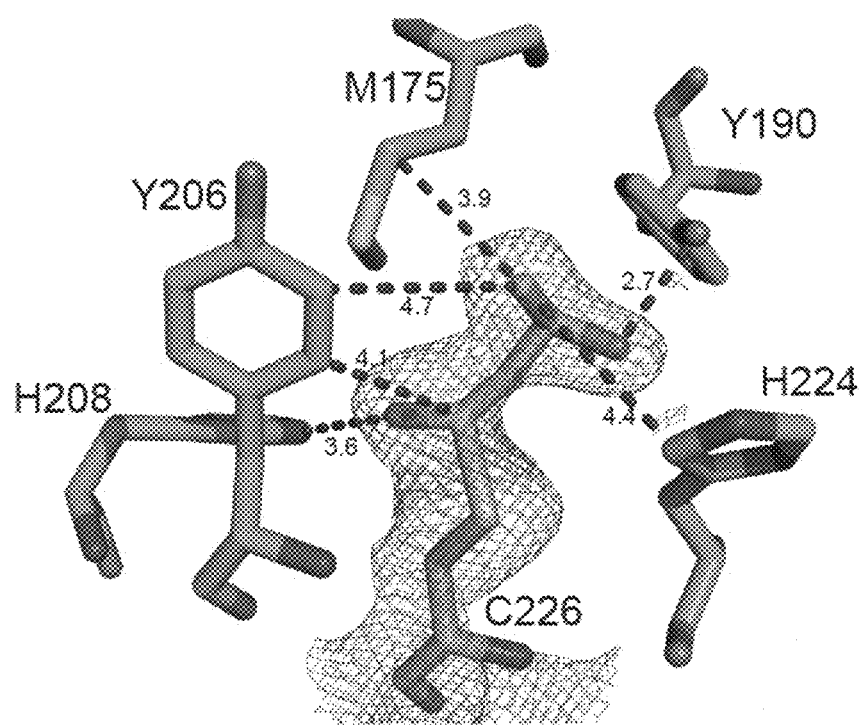
Figure 2C:
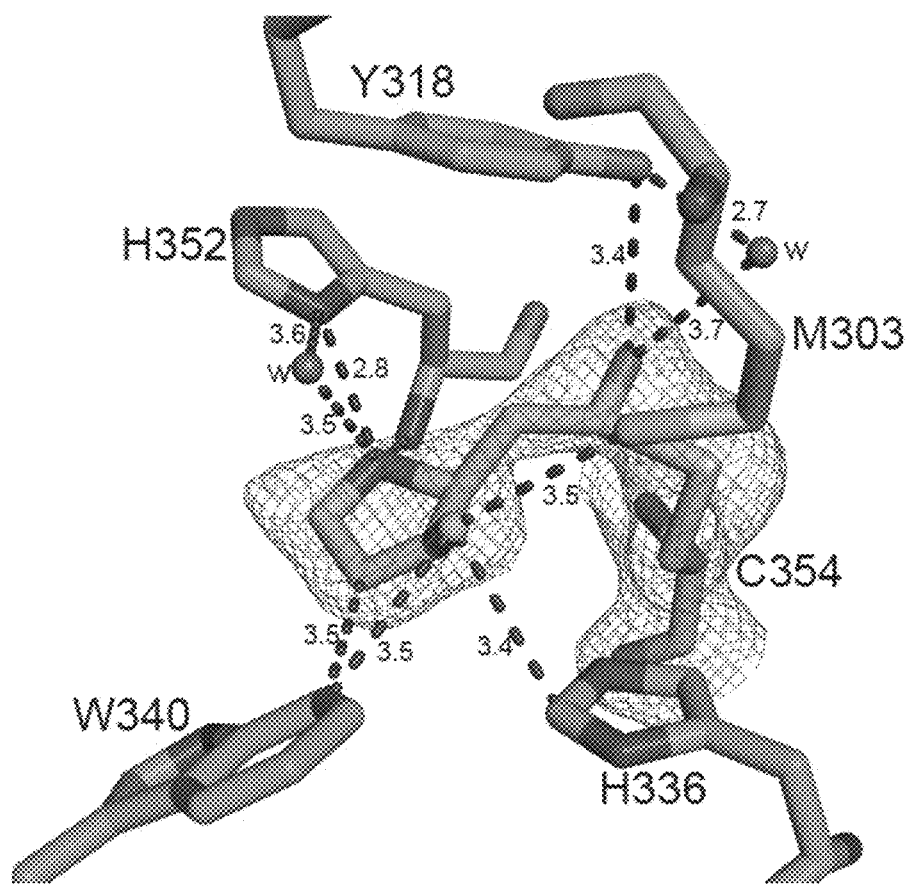

The in vitro and in vivo data indicated that penems and carbapenems have high potential for use in TB treatment. Understanding the specific molecular interactions responsible for the anti-TB activity of these β-lactams is critical for maximizing their therapeutic capacity. To discern the basis of the preferential binding of the M. tuberculosis L,D-transpeptidases with (carba)penems over other β-lactams, the crystal structures of $Ldt_{Mt2}$ in complex with faropenem and doripenem and $Ldt_{Mt1}$ with faropenem were solved (FIG. 2A-C). The catalytic core of $Ldt_{Mt2}$ is flanked by two cavities, an inner and outer. The faropenem adduct is bound in the inner cavity of the $Ldt_{Mt2}$ active site; this adduct lacked the β-lactam ring, the adjoining 5-membered ring and the R1 group initially present in the drug (FIG. 2A). Based on these data and the 86 Da adduct detected in UPLC-MS (Table 1), a 4-carbon derivative fragment of faropenem was built into the electron density. The carbonyl carbon, originally C7, was covalently bound to the sulfur of Cys354, and the carbonyl oxygen had electrostatic interactions with the backbone amide nitrogen of His352. The hydroxyethyl substituent (R2) established hydrogen-bonding interactions with the side chain of Tyr318 (both direct and water mediated) and with the backbone carbonyl of Ser331. The carbon adjacent to the hydroxyethyl substituent also displayed hydrophobic packing with the β-carbon of His352. In the crystal structure of $Ldt_{Mt1}$ with faropenem, a 86 Da adduct covalently attached to the catalytic Cys226 (equivalent to Cys354 in $Ldt_{Mt2}$) at a 110° angle could be modeled into the density (FIG. 2B). Unlike with $Ldt_{Mt2}$, the same adduct established different interactions in the active site of $Ldt_{Mt1}$. His208 (equivalent to His336 of $Ldt_{Mt2}$) did not interact with the sulfur of Cys226 but instead engaged the carbonyl C7 oxygen in the faropenem adduct via electrostatic interactions. The hydroxyethyl side chain and the adjacent carbon of the adduct were stabilized by hydrophobic packing with two methylenes of the Met175 side chain and with the β-carbon of His224 (equivalent to His352 of $Ldt_{Mt2}$). In addition, the hydroxyl group of the adduct formed a hydrogen bond with the phenol side chain of Tyr190 (equivalent to Tyr318 of $Ldt_{Mt2}$).

The orientation of doripenem bound to $Ldt_{Mt2}$ differed from that of faropenem: the doripenem adduct of 123 Da (Table 1) bound covalently to Cys354 but extended into the outer cavity and interacted with Trp340 (FIG. 2C). Doripenem was highly rearranged, lacking its R1 and R2 substituents and its β-lactam ring opened (C7 bound to Cys354), and could be modeled into the electron density. In the outer cavity, the C2 methyl on the pyrrolidine ring and the adjacent carbon in that ring of the adduct demonstrated van der Waals interactions with Trp340. The side chain of Tyr318 and the backbone amide nitrogen of Cys354 formed hydrogen bonds with the carbonyl C7 oxygen. The amino N4 of the pyrrolidine ring formed a hydrogen bond with the side-chain of His352.

Validation of $Ldt_{Mt2}$ Binding with (Carba)Penems.

Based on the crystal structure data, as well as sequence conservation among known L,D-transpeptidases, amino acids that are directly involved in molecular interactions with (carba)penems were identified. To build upon this work and further assess the role of these enzyme residues, a series of $Ldt_{Mt2}$ constructs each with single amino acid mutations in predicted key residues (Tyr318, His336, His352 and Cys354) and used UPLC-MS to evaluate the interaction of each of these mutants with faropenem, and the carbapenems biapenem and tebipenem was generated (results not shown). Stable adducts could be detected for biapenem with wild-type $Ldt_{Mt2}$, but no adducts could be detected for any of the mutant proteins, indicating that all four amino acids were involved in binding biapenem. Faropenem and tebipenem failed to produce adducts with mutants H336N, H336A, C354S or C354A but did produce stable adducts with the Y318F, Y318A, and H352A (H352N with faropenem only). Further assessment by ITC indicated loss of binding of both faropenem and tebipenem to C354S, H336N, H352N and Y318F (results not shown), thus confirming the involvement of each of these residues in the binding of $Ldt_{Mt2}$ with (carba)penems.

Figure 2D:
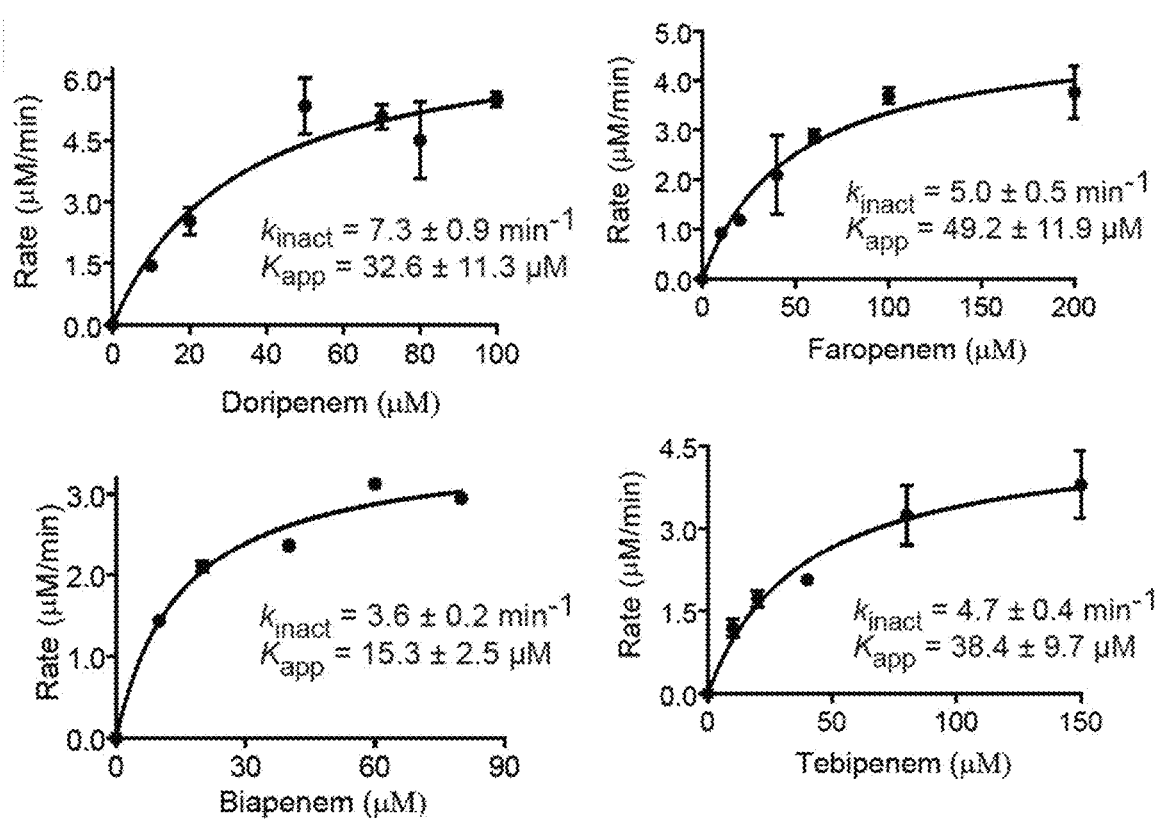

Since the UPLC-MS studies indicated irreversible acylation of $Ldt_{Mt2}$ by (carba)penems, spectroscopy-based assays were performed to calculate the rate of this irreversible inhibition. The $k_{inact}$ (maximum rate at which an irreversible transformation to enzyme-inhibitor complex occurs) and $K_{app}$ (inhibitor concentration required to achieve half maximum velocity) were determined by non-linear regression. These parameters demonstrated variations in the acylation kinetics for faropenem and each of the carbapenems (FIG. 2D). The efficiency of these reactions was assessed by the $k_{inact}/K_{app}$ ratios of doripenem (0.22 $\mu M^{-1} \text{min}^{-1}$), biapenem (0.23 $\mu M^{-1} \text{min}^{-1}$), faropenem (0.10 $\mu M^{-1} \text{min}^{-1}$) and tebipenem (0.12 $\mu M^{-1} \text{min}^{-1}$). Although all of these β-lactams inactivated $Ldt_{Mt2}$ by acylation, there were differences in $k_{inact}$ and $K_{app}$ values that may be attributable to variations in the thioether side chain of these carbapenems; these variations may cause changes in the rates of both drug binding and subsequent acylation.

Design, Synthesis and Assessment of Evolved Carbapenems.

The structure-activity and mechanistic data regarding the interactions between L,D-transpeptidases and faropenem/carbapenems, as well the previously described crystal structure of meropenem (a carbapenem) bound to $Ldt_{Mt2}$ (Kim, et al., 2013), provided significant information to guide the design of new carbapenems with improved potential as anti-TB compounds. A key observation from the co-crystal structures was the absence of extensive contacts between the protein and the pyrrolidine-2-carboxamide thioether at C2. Without wishing to be bound to any one particular theory, it was thought that the R1 substituent pyrrolidine interacted mainly with the outer cavity and solvent (illustrated in FIG. 3A) and therefore could be used to modify the physiochemical properties to enhance attributes such as permeability and pharmacokinetic profile. The R1 chain was replaced with various groups identified by naive Bayesian machine-learning models as the most frequent sulfur substituents in M. tuberculosis growth inhibitors (Ekins, et al., 2013), and initially focused on the 2-substituted analogs of existing carbapenems with an emphasis on R1 substituent to disrupt critical residues in the catalytic site of L,D-transpeptidases. Synthesis of the final carbapenems followed a two-stage process (not shown) where the enol phosphate and thiol (or immediate precursor) were reacted to afford the desired thioether. The 4-nitrobenzyl ester protecting group was then cleaved to yield the desired carbapenem.

Of the fully synthetic carbapenems illustrated in FIG. 3B, twelve exhibited in vitro activity against *M. tuberculosis*, having minimum inhibitory concentration (MIC) values at the low or sub µg/mL level (results not shown); most of which were lower than the MIC values of meropenem, doripenem, biapenem, faropenem and tebipenem against *M. tuberculosis* (Kaushik, et al., 2015). For four of the synthesized carbapenems with the lowest MICs for *M. tuberculosis*, namely T205, T206, T208 (all MICs 1-2 µg/mL) and T210 (MIC 0.25-0.5 µg/mL), their specific binding interactions with $Ldt_{Mt1}$ and $Ldt_{Mt2}$ by UPLC-MS were evaluated (Table 1). Each of these evolved carbapenems reacted with these enzymes and formed covalent adducts, indicating retention of the carbapenem skeleton/framework by the enzymes. Next, to assess the stability of the evolved carbapenems T208 and T210 were reacted with $Ldt_{Mt2}$ and quantified the adducts at 1 and 24 hrs. No observable adduct degradation even at 24 hrs was found (results not shown). The $k_{inact}/K_{app}$ ratios of the $Ldt_{Mt2}$ interactions with T208 and T210 were 0.56 and 0.07 $min^{-1}$ $µM^{-1}$, respectively (FIG. 3C), indicating that these experimental carbapenems were effective acylators of $Ldt_{Mt2}$ and at least as efficient as meropenem (Kim, et al., 2013), doripenem, biapenem, faropenem and tebipenem (FIG. 2D) in inactivating the enzyme. The $Ldt_{Mt2}$ mutants Y318F, H336N, H352N and C354S all exhibited poor binding to T210 (results not shown), again indicating that these residues are key for productive binding to carbapenems.

To examine the potential broader antibacterial activity of these experimental carbapenems, their activity (i.e., determined the MICs) against *M. abscessus* and a full panel of ESKAPE pathogens: *E. faecalis, S. aureus, K. pneumoniae, A. baumannii, P. aeruginosa* and *E. cloacae* also was characterized (results not shown). While none of the experimental carbapenems inhibited the growth of *M. abscessus*, several of the compounds (T221, T222, T223 and T224) inhibited the growth of all pathogens except *P. aeruginosa*, which was inhibited by T123. Furthermore, compounds T205, T206, T208 and T210 reacted and formed acyl adducts with the L,D-transpeptidases from *M. abscessus* ($Ldt_{Mab1}$ only), *K. pneumoniae, E. cloacae* and *P. aeruginosa* (Table 1) and the acyl-adducts formed are similar to those observed with $Ldt_{Mt2}$ indicating these evolved carbapenems acylate varying L,D-transpeptidases from unrelated bacteria by a similar mechanism ($Ldt_{Pa}$ is an exception as a smaller adduct, +56 Da, is formed with T208). Thus, although the experimental carbapenems were designed for improved binding to the *M. tuberculosis* L,D-transpeptidases, several display potential for use as broader spectrum antibacterial agents.

Structures of $Ldt_{Mt2}$ in Complex with Evolved Carbapenems.

Figure 4A:
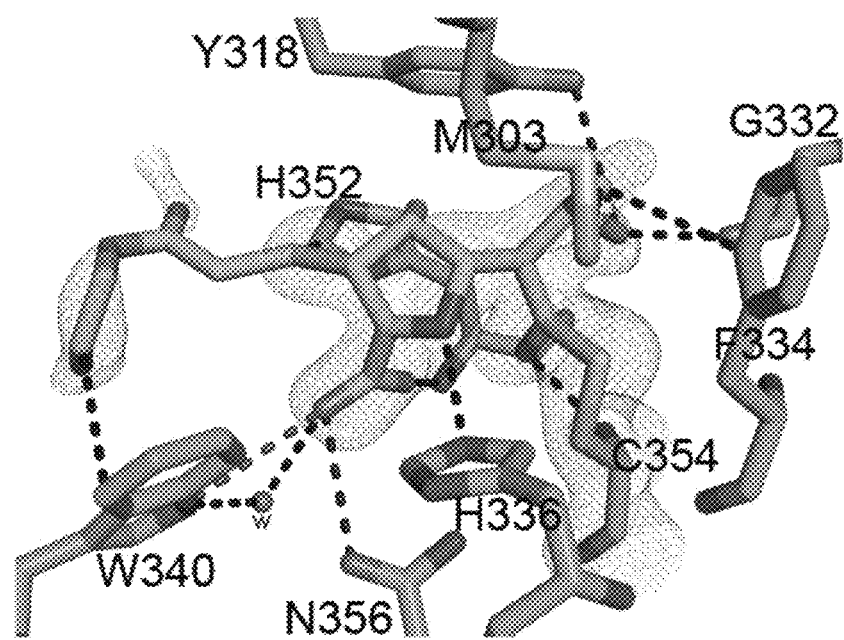
Figure 4B:
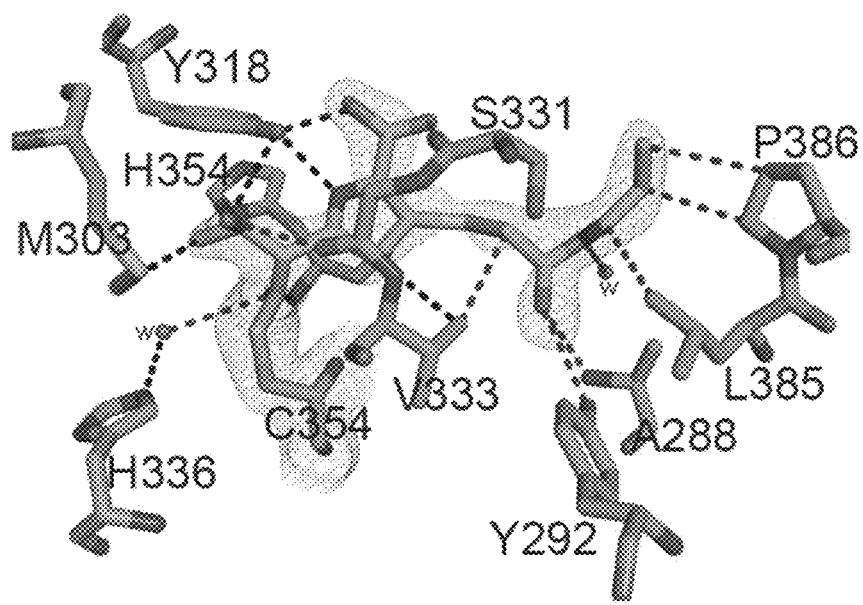
Figure 4C:
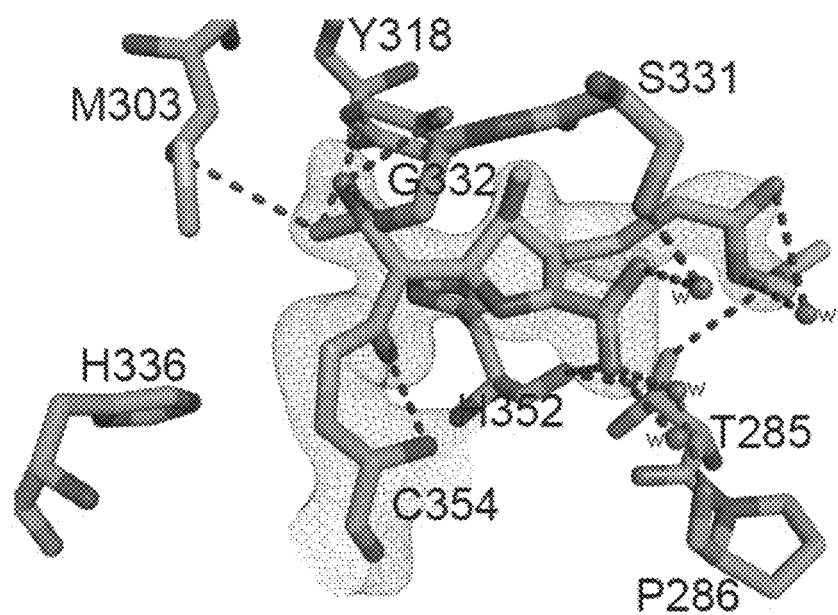

The evolved carbapenems also provided new insights to improve the ability to maximize the antimicrobial, and specifically the anti-TB activity, of this class of drugs. The crystal structures of $Ldt_{Mt2}$ in complex with T206, T208, T210 and T224 were therefore solved (FIG. 4). T206 binds in three different orientations in the active site of the enzyme, via the outer cavity (conformation A1) or via the inner cavity (conformation A2 and B), from two different crystal structure forms, $Ldt_{Mt2}$-T206-A and $Ldt_{Mt2}$-T206-B, In $Ldt_{Mt2}$-T206-A, the electron density map of T206 in conformation A1 in chain A shows this carbapenem interacting with the outer cavity and covalently attached to the catalytic Cys354 (FIG. 4A). The electron density of carbapenem T206 is contiguous to the $S^\gamma$ atom of Cys354, but it is missing for much of the R1 group beyond the thioether sulfur. The hydroxyl of the R2 group hydrogen bonds with the side chain of Tyr318 and displayed both a direct and a water-mediated hydrogen bond with the backbone carbonyl of Gly332. The carboxyl group at C3 of the pyrrolidine ring forms a hydrogen bond with the side chain of Trp340 and with the backbone amide of His352. Trp340 also has hydrophobic interactions with the alkyl tail of the R1 group of T206. In conformation A2, chain B of $Ldt_{Mt2}$-T206-A, T206 is bound in the inner cavity resembling the meropenem-bound structure (PDB ID 3VYP) (Li, et al., 2013), but the R2 group tail makes additional extensive electrostatic and hydrophobic interactions with Ala288, Tyr292, Leu385 and Pro386 (FIG. 4B). The C3 carboxyl group accepts a hydrogen bond from Tyr318, and Met303 has a hydrophobic interaction with the terminal carbon of the C6 hydroxyethyl side chain. From the crystal structure form $Ldt_{Mt2}$-T206-B, in conformation B of chain A, the carbonyl C7 (of what was the β-lactam ring) is covalently bound to Cys354, with the rest of the molecule extending into the inner cavity of the active site (FIG. 4C), similar to previous crystal structures of the meropenem:$Ldt_{t2}$ complexes (Kim, et al., 2013). The pyrrolidine ring and its carboxylate substituent have a conformation similar to the corresponding substructure of meropenem in chain A (PDB ID: 4GSU) (Kim, et al., 2013) and in conformation A of chain A (PDB ID: 3VYP) (Li, et al., 2013), but this ring was rotated with respect to the orientation observed in the other chains of 4GSU and 3VYP. Interestingly, T206 is fully ordered in conformation B, with its R1 group tail stabilized by hydrophobic interactions with residue Thr285 and by a network of water-mediated hydrogen bonds between the carboxylate of T206 and the side-chain Ser331, the backbone amide nitrogen of Ala288, and the backbone carbonyl oxygen of Pro286.

Figure 4D:
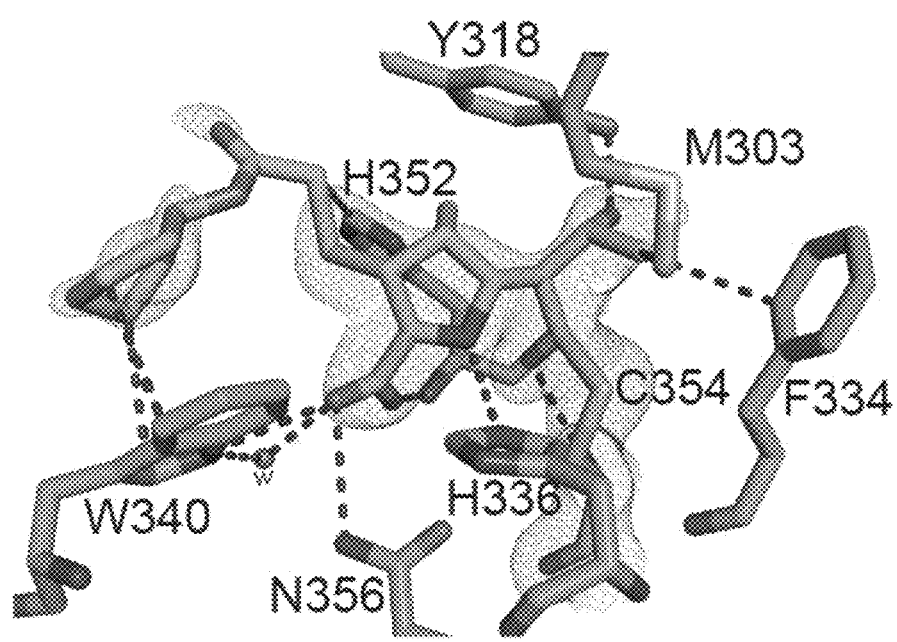
Figure 4E:
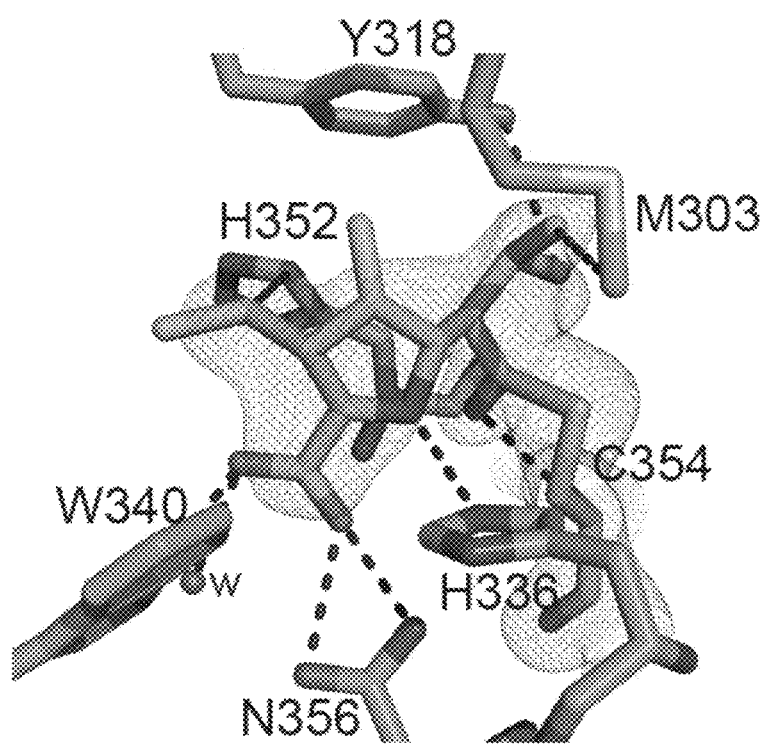
Figure 4F:
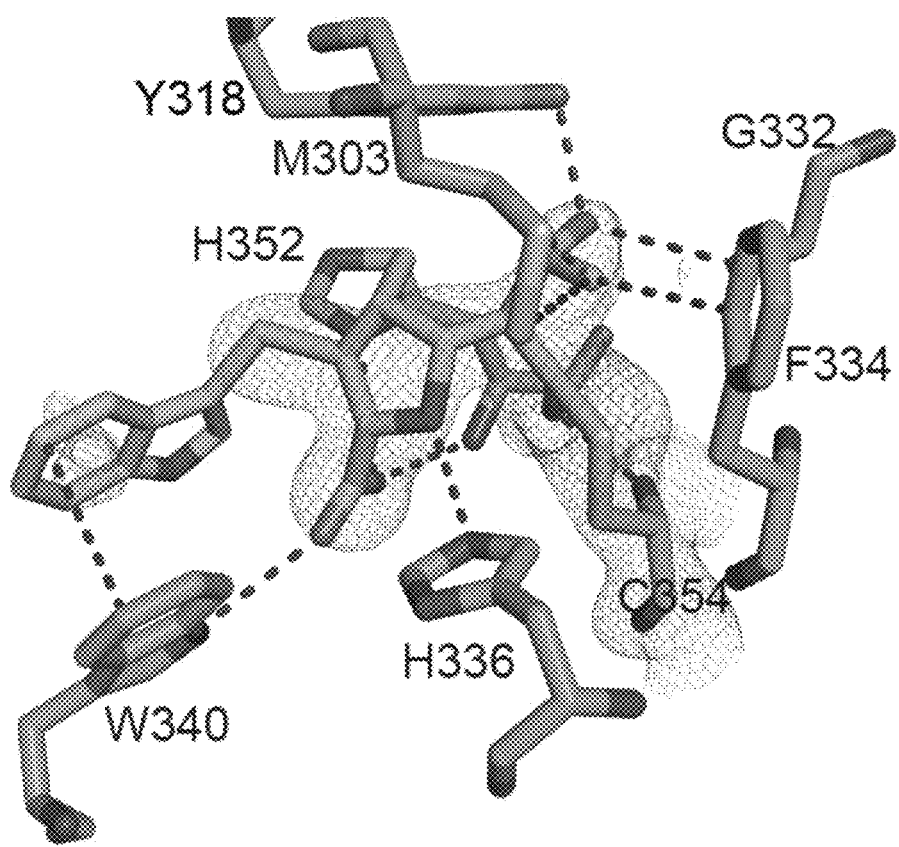

In the crystal structure of $Ldt_{Mt2}$ with T208, T210 and T224, the maps showed electron density for the respective inhibitors (and specifically the carbonyl carbon of what was the β-lactam moiety) within the distance necessary for covalent bonding to C354 (FIG. 4D, FIG. 4E, and FIG. 4F). T208, T210 and T224 extended into the outer cavity in a manner similar to conformation A of T206 and that of imipenem with $Ldt_{Mt1}$ (PDB ID: 4JMX) (Correale, et al., 2013). The conserved region of T208, T210 and T224 forms the same quaternary interactions with the outer cavity of $Ldt_{Mt2}$, and their C3 carboxyl accepts hydrogen bonds from Trp340 and Asn356 side chains thereby mimicking those found in T206 conformation A1. In all of the evolved carbapenems bound in the outer cavity, electron densities for the methyl group of the pyrrolidine ring at C1 position and the R1 group tail beyond the thioether sulfur are missing.

Example 4

Discussion

The traditionally understood targets of β-lactams are D,D-transpeptidases. Likewise, resistance to β-lactams has traditionally been attributed to β-lactamases, most of which have evolved as soluble β-lactam hydrolases from their membrane-bound D,D-transpeptidase ancestors (Meroueh, et al., 2003). However, L,D-transpeptidases are biochemically and structurally distinct from D,D-transpeptidases and use cysteine to catalyze the formation of non-classical 3→3 linkages in the peptidoglycan and thereby provide an alternative mechanism by which bacteria can survive in the presence of traditional D,D-transpeptidase-targeting β-lactams (Mainardi, et al., 2005). Therefore, molecules that can also target the L,D-transpeptidases have significant potential as agents with bactericidal activity against organisms that utilize both classical and non-classical transpeptidases when causing human disease.

Here, it has been demonstrated that penem and carbapenem β-lactam antibacterials have potent anti-TB activity using a preclinical mouse model of TB treatment. The bioavailability of many carbapenems is sub-optimal due to metabolism by dehydropepetidase-1 (DHP-1) in the renal proximal tubules (Hikida, et al., 1992). Faropenem and early carbapenems meropenem and imipenem exhibit limited activity in mice infected with $M.$ $tuberculosis$ (Dhar, et al., 2015; Chambers, et al., 2005; Veziris, et al., 2011; England, et al., 2012). A recent clinical trial (NCT02349841) demonstrated a promising early bactericidal activity of meropenem in TB patients (Diacon, et al., 2016). Compared to meropenem, biapenem is more potent against $M.$ $tuberculosis$ (Kaushik, et al., 2015) and is resistant to inactivation by DHP-1 (Hikida, et al., 1992). The anti-tubercular activity seen in the mouse model in this work suggests that new and evolved (carba)penems have promise in treatment of TB. In pursuit of developing new carbapenems, an in-depth biochemical and structural analyses of (carba)penem interactions with $M.$ $tuberculosis$ L,D-transpeptidases was conducted allowing for the development of evolved carbapenems with improved anti-TB activity. The activities of the presently disclosed evolved compounds with other bacterial pathogens, including difficult-to-treat ESKAPE pathogens, also was characterized, thereby demonstrating their broad-spectrum antibacterial potential.

Experiments characterizing the interactions between faropenem and carbapenems with the *M. tuberculosis* L,D-transpeptidases $Ldt_{Mt1}$ and $Ldt_{Mt2}$, including analysis of co-crystal structures of drug-enzyme interactions, have provided data that allowed us to propose molecular mechanisms responsible for enzyme inhibition. The reaction of faropenem with $Ldt_{Mt2}$ and $Ldt_{Mt1}$, proposed in FIG. 5A, was rapid (FIG. 2D) and yielded the inactivated enzymes bearing only (R)-3-hydroxybutyryl covalently linked to the active site cysteine, Cys354 in $Ldt_{Mt2}$ (FIG. 2A) and Cys226 in $Ldt_{Mt1}$ (FIG. 2B). Nucleophilic attack by this cysteine on the reactive β-lactam is proposed to open the 4-membered ring followed by scission of the remaining thiazoline ring. Such a cleavage process is known in the analogous masked enol opening of clavulanic acid by seryl β-lactamases (Charnas, et al., 1978). The resulting imine/iminium species, again paralleling clavulanate cleavage, is proposed to hydrate to an aminal, whose facile retro-aldol scission affords the observed inactivated enzyme adduct.

In contrast, reaction of the carbapenem doripenem at the $Ldt_{Mt2}$ catalytic center (proposed in FIG. 5B) takes a different course, but not one driven by the formation of a stable (aromatic) pyrrole ring of unchanged oxidation state as expected. Instead, formation of the net two-electron reduced pyrrolinium adduct hydrogen-bonded to the nearby His352 was observed. Specifically, attack of the active site cysteine on the carbapenem carbonyl is proposed to form an imine/iminium species, which may decarboxylate to a stabilized ylid, analogous to the active form of the cofactor thiamin. After protonation, the resulting pyrrolinium may be captured by the adjacent thioether and the resulting bridged sulfonium species, either by attack of a nucleophile or by reversible release of the enamine and scavenge of the sulfonium ion, achieves both the required two-electron reduction and preservation of the C1 and C5 stereocenters evident in the crystal structure. Subsequent to these events, or earlier, precedented retro-aldol reaction can ensue to expel the hydroxyethyl side chain as acetaldehyde (Hugonnet, et al., 2009; Drawz, et al., 2010). While these proposals are in agreement with a mechanism of carbapenem-induced inhibition of $Ldt_{Mt2}$ derived from a theoretical free energy study (Silva, et al., 2015), the data provide direct evidence of additional cleavage and rearrangement mechanisms beyond the loss of the C6 hydroxymethyl group thought to be common to carbapenems (Kim, et al., 2013). This information expands design options for carbapenems having alternative modes of transpeptidase inactivation. It remains to be seen how these fragmentation pathways for doripenem and faropenem are implicit in their whole-cell efficacy against *M. tuberculosis.*

Evaluation of molecular interactions of (carba)penems with L,D-transpeptidases facilitated the development of evolved carbapenems. Although a few of these compounds have been synthesized previously (Fung-Tomc, et al., 1995; Natsugari, et al., 1983; Abe, et al., 1996; Seki, et al., 1996), their ability to target *M. tuberculosis* transpeptidases has not been described. Of note was the prevalence of active molecules with $—SCH_2CO_2R$ (R=$CH_3$, $CH_2CH_3$, $(CH_2)_2CH_3$, $CH(CH_3)_2$, $C(CH_3)_3$, $(CH_2)_3CH_3$, c-$C_6H_{12}$), as well as —S(2-pyridyl) moieties (FIG. 3B). Consistent detection of the entire drug molecule bound to enzymes from five different organisms (Table 1) suggests that acylation occurs through a similar mechanism of inactivation for each carbapenem (T205, T206, T208 and T210), which is further supported by crystal structure data of T206, T208, T210 and T224 with $Ldt_{Mt2}$ (FIG. 4, 5C). Superposition of existing carbapenems and T206 in all conformations at the active site of $Ldt_{Mt2}$ (not shown) shows that the R1 sidechain of T206 establishes additional interactions with residues in the outer and inner cavities. In the inner cavity, the R1 sidechain is either stabilized by Pro386 or Thr285 accounting for why the R1 tail is ordered in the crystal structure (FIG. 4B and FIG. 4C). In the outer cavity, the R1 tail makes weak interactions with Trp340 as evidenced by the partial electron density (FIG. 4A).

Understanding how (carba)penems target L,D-transpeptidases is of critical importance for maximizing their potential for use in TB treatment, as these enzymes are not targeted by other anti-TB drugs, and therefore could play significant roles in the treatment of drug-resistant TB where new treatment options are greatly needed. A few clinical reports exist regarding the use of meropenem in combination with the β-lactamase inhibitor clavulanate in patients with multidrug-/extensively drug-resistant TB (Palmero, et al., 2015; Payen, et al., 2012; De Lorenzo, et al., 2013), although the direct impact of the carbapenem on treatment outcome could not be clearly assessed from these reports. Finally, this work has shown promising activity of carbapenems against each category of ESKAPE organisms, which represent difficult-to-treat, often nosocomially-transmitted bacterial pathogens for which new treatment options are also immediately needed. Thus, advancing knowledge of (carba)penem-based inhibition of bacterial transpeptidases impacts not only TB treatment, but also provide a rich source of new antibacterial agents effective against resistant organisms evolved to use 3→3 crosslinks in their cell walls. Bioinformatics/comparative genomics show that orthologs of the five L,D-transpeptidase genes in *M. tuberculosis* are widely distributed among bacterial pathogens and thus pose the threat of a genetic reservoir of antibiotic resistance that can now be recognized and blunted. The presence of multiple genes encoding D,D-transpeptidases, L,D-transpeptidases and β-lactamase in *M. tuberculosis* genome underscores their importance in peptidoglycan metabolism in this organism. Enzymes in each class, while similar in sequence, have distinct structures. Therefore, there is a continuum of structural variations around a similar function/theme. This is directly reflected in the varying affinities for different β-lactam structures in each sub-class. Again, without being bound to any one particular theory, it was thought that a combination of β-lactams that are effective against each enzyme class will be necessary to bring about a simultaneous inhibition of the enzymes and subsequently a total inhibition of peptidoglycan metabolism.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Abe, T., Hayashi, K., Isoda, T. & Kumagai, T. 2-((pyridyl-substituted)thio)-carbapenem derivative. Japan patent JP19940170499 19940630 (1996).

Brenek, S. J. et al. Development of a practical and convergent process for the preparation of sulopenem. *Org. Process Res. Dev.* 16, 1348-1359 (2012).

Chambers, H. F., Turner, J., Schecter, G. F., Kawamura, M. & Hopewell, P. C. Imipenem for treatment of tuberculosis in mice and humans. *Antimicrobial agents and chemotherapy* 49, 2816-2821, doi:10.1128/AAC.49.7.2816-2821.2005 (2005).

Charnas R L, Fisher J, Knowles J R. Chemical studies on the inactivation of *Escherichia coli* RTEM beta-lactamase by clavulanic acid. Biochemistry 1978; 17:2185-9.

Cordillot, M. et al. In vitro cross-linking of peptidoglycan by *Mycobacterium tuberculosis* L,D-transpeptidases and inactivation of these enzymes by carbapenems. *Antimicrobial agents and chemotherapy*, doi:10.1128/AAC.01663-13 (2013).

Correale, S., Ruggiero, A., Capparelli, R., Pedone, E. & Berisio, R. Structures of free and inhibited forms of the L,D-transpeptidase $Ldt_{Mt1}$ from *Mycobacterium tuberculosis*. *Acta crystallographica. Section D, Biological crystallography* 69, 1697-1706, doi:10.1107/S0907444913013085 (2013).

De Lorenzo, S. et al. Efficacy and safety of meropenem-clavulanate added to linezolid-containing regimens in the treatment of MDR-/XDR-TB. *The European respiratory journal* 41, 1386-1392, doi:10.1183/09031936.00124312 (2013).

Desmond E. Susceptibility Testing of Mycobacteria, Nocardiae and Other Aerobic Actinomycetes, Int (ed), *Association of Public Health Laboratories*. 2011

Dhar, N. et al. Rapid Cytolysis of *Mycobacterium tuberculosis* by Faropenem, an Orally Bioavailable β-Lactam Antibiotic. *Antimicrobial agents and chemotherapy* 59, 1308-1319, doi:10.1128/AAC.03461-14 (2015).

Diacon, A. H. et al. β-Lactams against Tuberculosis—New Trick for an Old Dog? *The New England journal of medicine* 375, 393-394, doi:10.1056/NEJMc1513236 (2016).

Drawz, S. M. et al. Inhibition of the class C β-lactamase from *Acinetobacter* spp.: insights into effective inhibitor design. *Biochemistry* 49, 329-340, doi:10.1021/bi9015988 (2010).

Ekins, S. et al. Enhancing Hit Identification in *Mycobacterium tuberculosis* Drug Discovery Using Validated Dual-Event Bayesian Models. *PloS one* 8, e63240 (2013).

England, K. et al. Meropenem-clavulanic acid shows activity against *Mycobacterium tuberculosis* in vivo. *Antimicrobial agents and chemotherapy* 56, 3384-3387 (2012).

Erdemli S B, Gupta R, Bishai W R, Lamichhane G, Amzel L M, Bianchet M A. Targeting the cell wall of *Mycobacterium tuberculosis*: structure and mechanism of L,D-transpeptidase 2. Structure 2012; 20:2103-15.

Fung-Tomc, J. C. et al. Structure-activity relationships of carbapenems that determine their dependence on porin protein D2 for activity against *Pseudomonas aeruginosa*. *Antimicrobial agents and chemotherapy* 39, 394-399 (1995).

Gavan T L, Town M A. A microdilution method for antibiotic susceptibility testing: an evaluation. *American journal of clinical pathology*. 53, 880-5 (1970).

Gupta R, Lavollay M, Mainardi J L, Arthur M, Bishai W R, Lamichhane G. The *Mycobacterium tuberculosis* protein LdtMt2 is a nonclassical transpeptidase required for virulence and resistance to amoxicillin. Nature medicine 2010; 16:466-9.

Hikida, M., Kawashima, K., Yoshida, M. & Mitsuhashi, S. Inactivation of new carbapenem antibiotics by dehydropeptidase-I from porcine and human renal cortex. *The Journal of antimicrobial chemotherapy* 30, 129-134 (1992).

Hugonnet J E, Tremblay L W, Boshoff H I, Barry C E, 3rd, Blanchard J S. Meropenem-clavulanate is effective against extensively drug-resistant *Mycobacterium tuberculosis*. Science (New York, N.Y. 2009; 323:1215-8).

Kaushik A, Makkar N, Pandey P, Parrish N, Singh U, Lamichhane G. Carbapenems and Rifampin Exhibit Synergy against *Mycobacterium tuberculosis* and *Mycobacterium abscessus*. Antimicrobial agents and chemotherapy 2015; 59:6561-7.

Kim, H. S. et al. Structural basis for the inhibition of *Mycobacterium tuberculosis* L,D-transpeptidase by meropenem, a drug effective against extensively drug-resistant strains. *Acta crystallographica. Section D, Biological crystallography* 69, 420-431 (2013).

Kumar P, Arora K, Lloyd J R, et al. Meropenem inhibits D,D-carboxypeptidase activity in *Mycobacterium tuberculosis*. Molecular microbiology 2012; 86:367-81.

Lavollay M, Arthur M, Fourgeaud M, et al. The peptidoglycan of stationary-phase *Mycobacterium tuberculosis* predominantly contains cross-links generated by L,D-transpeptidation. Journal of bacteriology 2008; 190:4360-6.

Li, W. J. et al. Crystal structure of L,D-transpeptidase $Ldt_{Mt2}$ in complex with meropenem reveals the mechanism of carbapenem against *Mycobacterium tuberculosis*. Cell research 23, 728-731 (2013).

Mainardi J L, Fourgeaud M, Hugonnet J E, et al. A novel peptidoglycan cross-linking enzyme for a beta-lactam-resistant transpeptidation pathway. The Journal of biological chemistry 2005; 280:38146-52.

Meroueh, S. O., Minasov, G., Lee, W., Shoichet, B. K. & Mobashery, S. Structural aspects for evolution of β-lactamases from penicillin-binding proteins. *Journal of the American Chemical Society* 125, 9612-9618, doi:10.1021/ja034861u (2003).

Natsugari, H., Matsushita, Y., Yoshioka, K. & Matsui, S. 5,6-cis-carbapenem-3-carboxylic acid derivatives and process for their preparation. Japan patent (1983).

Palmero, D. et al. First series of patients with XDR and pre-XDR TB treated with regimens that included meropenen-clavulanate in Argentina. *Archivos de bronconeumologia* 51, e49-52, doi:10.1016/j.arbres.2015.03.012 (2015).

Payen, M. C. et al. Clinical use of the meropenem-clavulanate combination for extensively drug-resistant tuberculosis. *Int J Tuberc Lung Dis* 16, 558-560 (2012).

Rotilie C A, Fass R J, Prior R B, Perkins R L. Microdilution technique for antimicrobial susceptibility testing of anaerobic bacteria. *Antimicrobial agents and chemotherapy.* 7, 311-15 (1975).

Rullas, J. et al. Combinations of β-lactam antibiotics currently in clinical trials are efficacious in a DHP-I deficient mice model of TB infection. *Antimicrobial agents and chemotherapy*, doi:10.1128/AAC.01063-15 (2015).

Schoonmaker, M. K., Bishai, W. R. & Lamichhane, G. Nonclassical transpeptidases of *Mycobacterium tuberculosis* alter cell size, morphology, the cytosolic matrix, protein localization, virulence, and resistance to β-lactams. *Journal of bacteriology* 196, 1394-1402, doi:10.1128/JB.01396-13 (2014).

Seki, M., Kondo, K. & Iwasaki, T. Efficient synthesis of 1β-methylcarbapenems based on the counter-attack strategy. *Journal of the Chemical Society, Perkin Transactions* 1 2851-2856 (1996).

Silva, J. R. et al. Targeting the cell wall of *Mycobacterium tuberculosis*: A molecular modelling investigation of the interaction of imipenem and meropenem with L,D-transpeptidase 2. *Journal of biomolecular structure & dynamics*, 1-34, doi:10.1080/07391102.2015.1029000 (2015).

Veziris, N., Truffot, C., Mainardi, J. L. & Jarlier, V. Activity of carbapenems combined with clavulanate against murine tuberculosis. *Antimicrobial agents and chemotherapy* 55, 2597-2600 (2011).

Walsh C. Antibiotics: Actions, Origins, Resistance. Washington D.C.: ASM Press, 2003 (Walsh C, ed.).

WHO. Global Tuberculosis Report. Geneva: World Health Organization, 2015.

Wivagg, C. N., Bhattacharyya, R. P. & Hung, D. T. Mechanisms of β-lactam killing and resistance in the context of *Mycobacterium tuberculosis*. *The Journal of antibiotics* 67, 645-654, doi:10.1038/ja.2014.94 (2014).

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (Ic), or stereoisomers or pharmaceutically acceptable salts thereof:

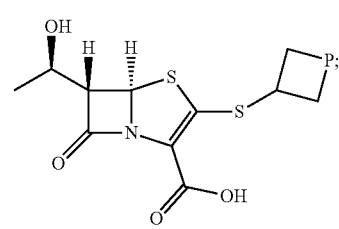

(Ic)

wherein
P is —N($R_6$)—; and
$R_6$ is

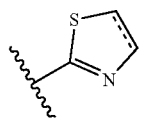

2. The compound of claim 1, wherein the compound of formula (Ic) is:

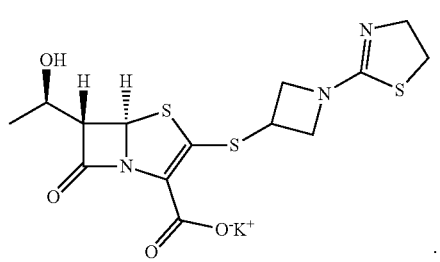

(T405)

3. A method of treating, or preventing a bacterial infection in a subject comprising administering to the subject a therapeutically effective amount of a compound of claim 1, stereoisomer, or pharmaceutically acceptable salt thereof.

4. The method of claim 3, wherein the bacterial infection is selected from the group consisting of *M. tuberculosis, M. abscessus, A. baumannii, S. aureus, K. pneumoniae, E. cloacae, P. aeruginosa* and *E. faecalis* or a combination thereof.

5. The method of claim 3, wherein the bacterial infection is one or more strains of bacteria that is resistant to antimicrobial agents directed to inactive D, D-transpeptidase.

6. A method of inhibiting the growth of a bacterium in vitro comprising contacting the bacterium with an effective amount of a compound of claim 1, stereoisomer, or pharmaceutically acceptable salt thereof.

7. A method of inhibiting L,D-transpeptidase activity in a subject with a bacterial infection, comprising administering to the subject an effective amount of a compound of claim 1, stereoisomer, or pharmaceutically acceptable salt thereof.

8. The method according to claim 3, wherein the subject is a human.

9. A pharmaceutical composition comprising a compound of claim 1 and a pharmaceutically acceptable carrier.

10. The pharmaceutical composition of claim 9, wherein the pharmaceutical composition comprises one or more other antimicrobial compound.

11. The method according to claim 7, wherein the subject is a human.

12. The method of claim 3, wherein the compound is:

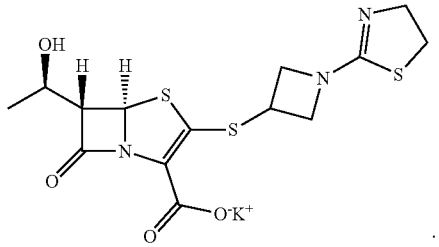
(T405)

13. The method of claim 6, wherein the compound is:

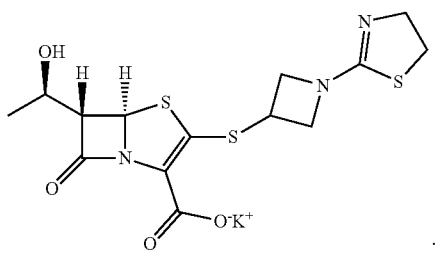
(T405)

14. The method of claim 7, wherein the compound is:

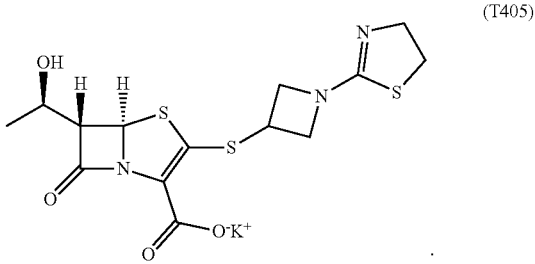
(T405)

15. The pharmaceutical composition of claim 9, wherein the compound is:

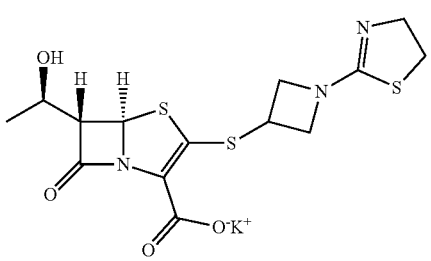
(T405)

* * * * *